US006815542B2

(12) United States Patent
Hong et al.

(10) Patent No.: US 6,815,542 B2
(45) Date of Patent: Nov. 9, 2004

(54) NUCLEOSIDE COMPOUNDS AND USES THEREOF

(75) Inventors: Zhi Hong, Aliso Viejo, CA (US); Jean-Luc Girardet, Aliso Viejo, CA (US); Kanda Ramasamy, Aliso Viejo, CA (US); Johnson Lau, Newport Beach, CA (US)

(73) Assignee: Ribapharm, Inc., Costa Mesa, CA (US)

( * ) Notice: Subject to any disclaimer, the term of this patent is extended or adjusted under 35 U.S.C. 154(b) by 0 days.

(21) Appl. No.: 10/318,476

(22) Filed: Dec. 13, 2002

(65) Prior Publication Data

US 2004/0002596 A1 Jan. 1, 2004

Related U.S. Application Data

(63) Continuation-in-part of application No. 09/594,410, filed on Jun. 16, 2000, now Pat. No. 6,495,677.

(51) Int. Cl.$^7$ ...................... C07H 19/04; C07H 19/052; C07H 19/056

(52) U.S. Cl. ...................... 536/28.6; 536/28.7; 536/28.8

(58) Field of Search ............................ 536/28.6, 28.7, 536/28.8

(56) References Cited

U.S. PATENT DOCUMENTS

| | | | | | |
|---|---|---|---|---|---|
| 3,798,209 | A | * | 3/1974 | Witkowski et al. | 536/26.9 |
| 3,984,396 | A | * | 10/1976 | Witkowski et al. | 536/26.11 |
| 3,991,078 | A | * | 11/1976 | Witkowski et al. | 548/266.8 |
| 4,093,624 | A | * | 6/1978 | Revankar et al. | 548/130 |
| 6,130,326 | A | * | 10/2000 | Ramasamy et al. | 536/28.7 |
| 6,495,677 | B1 | * | 12/2002 | Ramasamy et al. | 536/28.6 |

* cited by examiner

Primary Examiner—James O. Wilson
Assistant Examiner—Howard V. Owens, Jr.
(74) Attorney, Agent, or Firm—Brown, Raysman, Millstein, Felder & Steiner, LLP

(57) ABSTRACT

Nucleosides, novel nucleoside analog compounds and their novel prodrug forms are disclosed. The novel compounds, prodrugs, or pharmaceutically acceptable esters or salts thereof may be used in pharmaceutical compositions, and such compositions may be used to treat an infection, an infestation, a neoplasm, or an autoimmune disease. The novel compounds may also be used to modulate aspects of the immune system, including modulation of Type 1 and Type 2 activity.

6 Claims, 2 Drawing Sheets

FIGURE 1 - The effect of viramidine, ribavirin and levovirin on Type 1 cytokine synthesis in SEB-activated human T cells

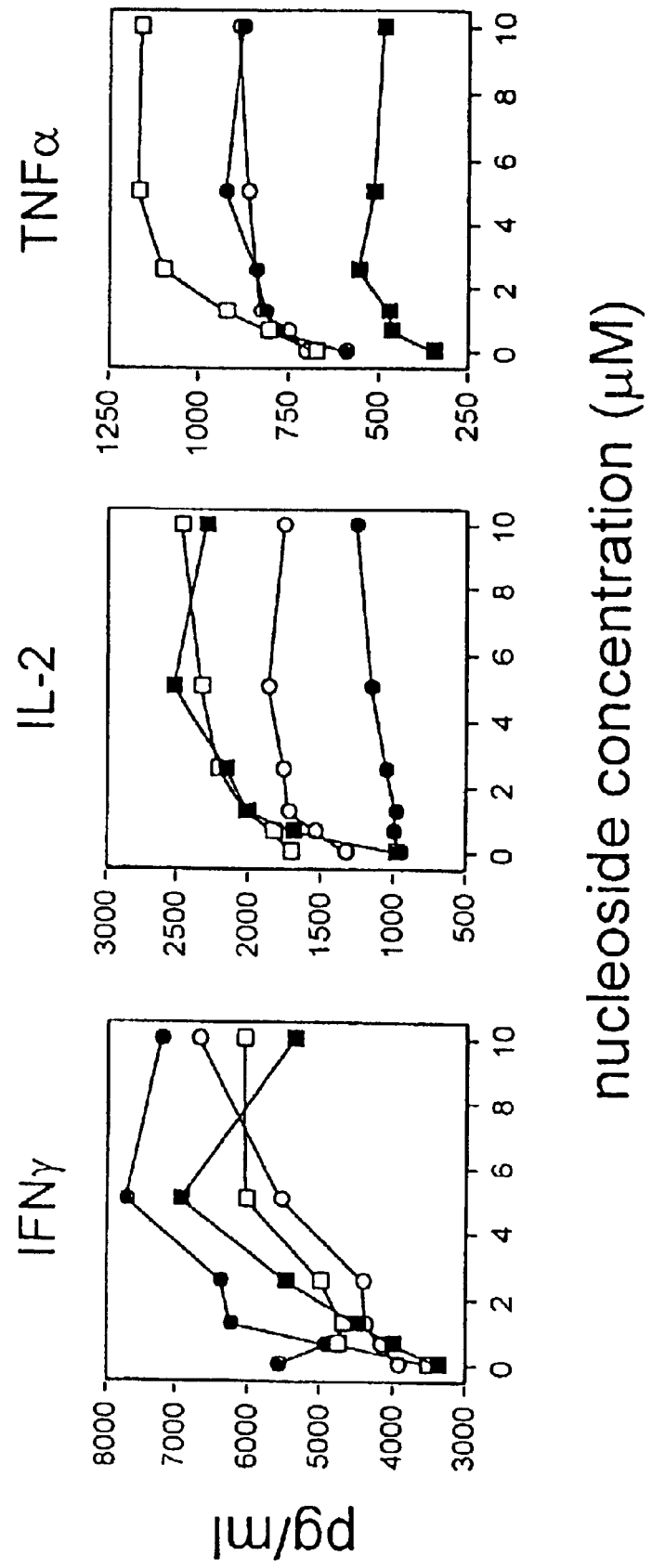
FIGURE 2 - The effect of 0.625 - 10µM viramidine on Type 1 cytokine synthesis in SEB-activated human T cells

US 6,815,542 B2

NUCLEOSIDE COMPOUNDS AND USES THEREOF

This application is a continuation-in-part of allowed U.S. application, Ser. No. 09/594,410, filed Jun. 16, 2000, now U.S. Pat. No. 6,495,677, which is incorporated herein by reference.

FIELD OF THE INVENTION

The present invention relates to the field of nucleoside analogs.

BACKGROUND OF THE INVENTION

Ribavirin (1-β-D-ribofuranosyl-1,2,4-triazole-3-carboxamide) is a nucleoside analog that has demonstrated efficacy in treating viral diseases both as monotherapy (respiratory syncytial virus, Hall, C. B.; McBride, J. T.; Walsh, E. E.; Bell, D. M.; Gala, C. L.; Hildreth, S.; Ten Eyck, L. G.; W. J. Hall. Aerosolized Ribavirin treatment of infants with respiratory syncytial viral infection. *N. Engl. J. Med.* 1983, 308, 1443–1447), and in combination therapy with interferon-alpha (hepatitis C virus, Reichard, O.; Norkrans, G.; Fryden, A.; Braconier, J-H.; Sonnerborg, A.; Weiland, O. Randomized, double blind, placebo controlled trial of interferon alpha 2B with and without Ribavirin for chronic hepatitis C. *Lancet* 1998, 351, 83–87).

Recently reported studies indicate that the in vivo utility of Ribavirin can result not only from direct inhibition of viral replication, but also from its ability to enhance T cell-mediated immunity (Hultgren, C.; Milich, D. R.; Weiland, O.; Sällberg, M. The antiviral compound Ribavirin modulates the T helper Type1/Type2 subset balance in hepatitis B and C virus-specific immune responses. *J. Gen. Virol.* 1998, 79, 2381–2391; Ning, Q.; Brown, D.; Parodo, J.; Cattral, M.; Fung, L.; Gorczynski, R.; Cole, E., Fung, L.; Ding, J. W.; Liu, M. F.; Rotstein, O.; Phillips, M. J.; Levy, G. Ribavirin inhibits viral-induced macrophage production of tumor necrosis factor, interleukin-1, procoagulant activity fgl2 prothrombinase and preserves Th1 cytokine production but inhibits Th2 cytokine response. *J. Immunol.* 1998, 160, 3487–3493; Martin, M. J.; Navas, S.; Quiroga, J. A.; Pardo, M.; Carreno, V. Effects of the Ribavirin-interferon alpha combination on cultured peripheral blood mononuclear cells from chronic hepatitis C patients. *Cytokine* 1998, 79, 2381–2391). This immunomodulatory effect of Ribavirin is demonstrable in vitro by measuring the levels of Type 1 cytokines produced by activated T cells from both humans and mice (Tam, R. C.; Pai, B.; Bard, J.; Lim, C.; Averett, D. R.; Phan, U. T.; Milovanovic, T. Ribavirin polarizes human T cell responses towards a Type 1 cytokine profile. *J. Hepatol.* 1999, 30, 376–382) and by other measures. The induction of a Type 1 cytokine bias by Ribavirin is functionally significant in vivo in murine systems (Tam, R. C.; Lim, C.; Bard, J.; Pai, B. Contact hypersensitivity responses following Ribavirin treatment in vivo are influenced by Type 1 cytokine polarization, regulation of IL-10 expression and costimulatory signaling. *J. Immunol.* 1999, 163, 3709–3717).

Mammalian immune systems contain two major classes of lymphocytes: B lymphocytes (B cells), which originate in the bone marrow; and T lymphocytes (T cells) that originate in the thymus. B cells are largely responsible for humoral immunity (i.e., antibody production), while T cells are largely responsible for cell-mediated immunity. T cells are generally considered to fall into two subclasses, helper T cells and cytotoxic T cells. Helper T cells activate other lymphocytes, including B cells, cytotoxic T cells, and macrophages, by releasing soluble protein mediators called cytokines that are involved in cell-mediated immunity. As used herein, lymphokines are a subset of cytokines. Helper T cells are also generally considered to fall into two subclasses, Type 1 and Type 2. Type 1 cells produce interleukin 2 (IL-2), tumor necrosis factor (TNFα) and interferon gamma (IFNγ), and are responsible primarily for cell-mediated immunity such as delayed type hypersensitivity and antiviral immunity. In contrast, Type 2 cells produce interleukins, IL4, IL-5, IL-6, IL-9, IL-10 and IL-13, and are primarily involved in assisting humoral immune responses such as those seen in response to allergens, e.g. IgE and lgG4 antibody isotype switching (Mosmann, 1989, *Annu Rev Immunol,* 7:145–173).

As used herein, the terms Type 1 and Type 2 "responses" are meant to include the entire range of effects resulting from induction of Type 1 and Type 2 lymphocytes, respectively. Among other things, such responses include variation in production of the corresponding cytokines through transcription, translation, secretion, and possibly other mechanisms, increased proliferation of the corresponding lymphocytes, and other effects associated with increased production of cytokines, including motility effects.

Previous application Ser. Nos. (09/291903, 09/471513, 60/164365, 60/164366, 60/172097, 60/175111, and 60/189672), each of which is incorporated herein by reference, relate to aspects of our recent discoveries involving the effect of various nucleosides (which are defined herein to include derivatives and analogs of native nucleosides) on selectively modulating lymphocyte responses relative to each other. Among other things, we have shown that either of the Type 1 and Type 2 responses can be selectively suppressed while the other is either induced or left relatively unaffected, and either of the Type 1 or Type 2 responses can be selectively induced while the other is either suppressed or left relatively unaffected. We have also discovered the surprising fact that some nucleosides effective in selectively modulating Type 1 and Type 2 responses relative to one another tend to have a bimodal effect. Among other things, some nucleosides that tend to generally suppress or induce both Type 1 and Type 2 activity at a relatively higher dose tend to selectively modulate Type 1 and Type 2 relative to each other at relatively lower doses.

Viramidine™ (1-β-D-ribofuranosyl-1,2,4-triazole-3-carboxamidine hydrochloride) has been shown active in ten different viruses—comparable to Ribavirin. (J. T. Witkowski, R. K. Robins, G. P. Khare, R. W. Sidwell, *J. Med. Chem.,* 16, 935–937, 1973; R. W. Sidwell, J. H. Huffman, D. L. Barnard, D. Y. Pifat, *Antiviral Research,* 10, 193–208, 1988; B. Gabrielsen, M. J. Phelan, L. Barthel-Rosa, C. See, J. W. Huggins, D. F. Kefauver, T. P. Monath, M. A. Ussery, G. N. Chmumy, E. M. Schubert, K. Upadhya, C. Kwong, D. A. Carter, J. A. Secrist III, J. J. Kirsi, W. M. Shannon, R. W. Sidwell, G. D. Kini, R. K. Robins, *J. Med. Chem.,* 35, 3231–3238, 1992). In addition, Viramidine™, like Ribavirin, is an inhibitor of IMP dehydrogenase (R. C. Willis, R. K. Robins, J. E. Seegmiller, *Molecular Pharmacology,* 18, 287–295, 1980). Furthermore, preliminary toxicology studies suggest that Viramidine™ is less toxic than Ribavirin (D. Y. Pifat, R. W. Sidwell, P. G. Canonico, *Antiviral Research,* 9, 136, 1988). Also, recent studies at our lab (R. Tam, K. Ramasamy, ICN Pharmaceuticals, Inc., unpublished results, 1999) revealed that Viramidine™ and Ribavirin exhibit similar immunomodulatory properties. These results coupled with low bioavailability and the toxicity associated with Ribavirin prompt us not only to develop Viramidine™ for other viral diseases but also to prepare other derivatives of Viramidine™, including the synthesis of prodrugs of Viramidine™, and screen them as potential antiviral agents.

Ribavirin and Levovirin are similar with respect to structure, except that Levovirin is in the L-configuration of the compound and has a substantially reduced toxicity. For example, while oral administration of Ribavirin in rats at 180 mg/kg over four weeks produced significant hemolytic anemia and leukopenia, Levovirin did not produce any observable clinical pathology. Furthermore, it is contemplated that treatment of a viral disease with Levovirin is predominantly based on the modulation of the Th1/Th2 balance towards a Th1 dominated response, and not predominantly based on a direct antiviral effect. The term "direct antiviral" effect or activity as used herein refers to an immediate effect or activity of a drug on viral assembly or replication. In contrast, a reduction of viral activity or replication that is at least in part mediated by one or more components of the immune system is not considered a "direct antiviral" effect or activity. Likewise, it should be appreciated that a relative reduction of the Th2 response during a treatment may be especially advantageous in diseases that are correlated with an increased Th2 response (e.g., HCV infection).

The effect of other nucleoside analogs on selectively modulating lymphocyte responses relative to each other has not been previously studied or documented. We have discovered that the bimodal effect, or selective modulation of Type 1 and Type 2 responses relative to one another, also occurs after administration of other nucleoside analogs, such as pro-drug forms of the compounds.

There are many barriers to overcome in developing biologically active compounds into clinically useful agents. Many potent biologically active compounds never become clinically useful agents because of their undesirable biopharmaceutical properties which include low bioavailability due to low permeability through biological barriers, such as the blood brain barrier (BBB) and the intestinal barrier. Although many factors affect the bioavailability of a drug, the undesirable physicochemical properties (e.g., charge, lipophilicity, hydrogen bonding potential, size) of many drugs is probably one of the most commonly encountered factors that hinder the permeation of drugs through biological barriers. Therefore, optimization of the physicochemical characteristics (charge, lipophilicity, hydrogen bonding potential, size) of a drug is probably the most likely general strategy to facilitate the transport of drugs through such membrane barriers.

To optimize the physicochemical properties of drugs, one possible strategy is that of prodrugs. (H. Bundgaard, *Design of Prodrugs*, Elsevier, Amsterdam, 1985; N. Bodor, L. Prokai, W. M. Wu, H. Farag, S. Jonalagadda, M. Kawamura, J. Simpkins, *Science*, 257, 1698–1700, 1992; H. E. Taylor, K. B. Sloan, *J. Pharm. Sci*, 87, 5–20, 1998). The term prodrug is used to describe an agent, which must undergo chemical or enzymatic transformation to the active or parent drug after administration, so that the metabolic product or parent drug can subsequently exhibit the desired pharmacological response. By derivatizing certain polar functional groups in small organic molecules transiently and bioreversibly, the undesirable physicochemical characteristics (e.g., charge, hydrogen bonding potential) of these groups have been "masked" without permanently altering the pharmacological properties of the molecules. This strategy has been very successfully used in cases where the prodrug derivatization involves converting a carboxyl or a hydroxyl functional group into an ester, which can be readily hydrolyzed in vivo either chemically, or enzymatically.

Thus, although various prodrugs and modifications of triazole-nucleosides are known in the art, several potential disadvantages (e.g., limited bioavailability or limited selectivity towards a diseased cell and/or organ) still remain. Therefore, there is still a need to provide improved compositions and methods for triazole nucleosides.

SUMMARY OF THE INVENTION

The present invention is directed to nucleoside analogs and related compounds, including their prodrugs and metabolites, and their therapeutic uses and synthesis.

In one aspect of the invention, there are provided nucleosides, nucleoside analogs and nucleoside prodrugs of the generalized Formula below, in which the sugar is either in the L- or D-configuration:

R-Nu and wherein Nu is a nucleoside or nucleoside analog, and R, which may or may not be present, comprises a ligand, otherwise termed a substituent, that is designed to modify the nucleoside through modification of the sugar, the base, or in some cases both the sugar and the base.

In one aspect of the invention, there are provided nucleoside analogs and prodrugs of Formula 1, in which the sugar is either in the L- or D-configuration:

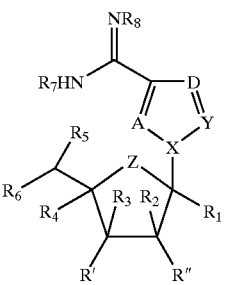

Formula 1 and wherein A, X, Y, and D are independently selected from N or C—$R_9$; $R_9$ is independently H, halogen, lower alkyl, alkenyl, alkynyl, amino, CN, SH, CHO, COOH, $CH_2OH$, or hydroxyl; Z is O, $CH_2$ or S; R' and R" are independently selected from H, hydroxyl, protected hydroxyl, or halogen; $R_1$, $R_2$, $R_3$, $R_4$, and $R_5$, are independently selected from H, halogens, CN, $CH_2OH$, lower alkyl, vinyl or acetylene; when $R_2$ is hydroxyl, then, R" that is attached to the same carbon as that of $R_2$ is not halogen; when $R_3$ is hydroxyl, then, R' that is attached to the same carbon as that of $R_3$ is not halogen; $R_6$ is independently selected from H, hydroxyl, protected hydroxyl, —$CH_2OH$, —$CH_2PO(OH)_2$—, O-amino acids, O-retinoic acid, O-cholesteral, O-cholic acid, O-coumarinic acid, O-salicylic acid, O-succinic acid, O-bile acid, O-lipids, O—P(O)—(O—$CH_2$—$CH_2$—S—CO—$CH_3$)$_2$; O-steroids; Boranophosphate, Boranophosphate derivatives, O-monophosphate derivatives, O-diphosphate derivatives or O-triphosphate derivatives; $R_7$ is independently selected from H, alkyl, $CH_3COO$—, $CH_3COO$-Phenyl-$CH_2$—O—CO—, phenyl, —($CH_2$)n-COOH, coumarinic acid, salicylic acid, dithiosuccinoyl derivatives, reductase mediated cleavable groups, phosphonoformic acid or phosphoramidates groups; $R_8$ is independently selected from H, H*HCl, H*HBr, lower alkyl, carbamate, phenyl, CH₃COO—, CH₃COO-Phenyl-CH₂—O—CO—, phenyl, or —(CH₂)n-COOH; R₇ and R₈ may form a cyclic structure or be independently an amino acid.

In another aspect of the invention, there are provided nucleoside analogs and prodrugs of Formula 2, in which the sugar is either in the L- or D-configuration:

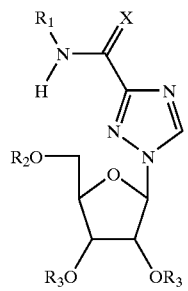

Formula 2 wherein X is O, NH; R₁ is H or a masking group of the amino group; R₂ is selected from H, HC(O)—, Boranophosphate, Boranophosphate derivative, R'—C(O)—, wherein R' is substituted or unsubstituted alkyl, substituted or unsubstituted alkenyl, substituted or unsubstituted alkynyl, or R₂ is a protected or unprotected monophosphate, diphosphate, or triphosphate, and R₃ is independently H or C1–C18 acyl.

In another aspect of the invention, there are provided nucleoside analogs and prodrugs of Formula 3, in which the sugar is either in the L- or D-configuration:

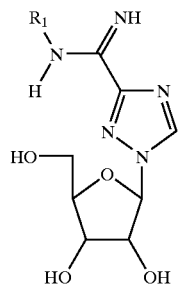

Formula 3 wherein R₁ is a masking group having any of the following structures:

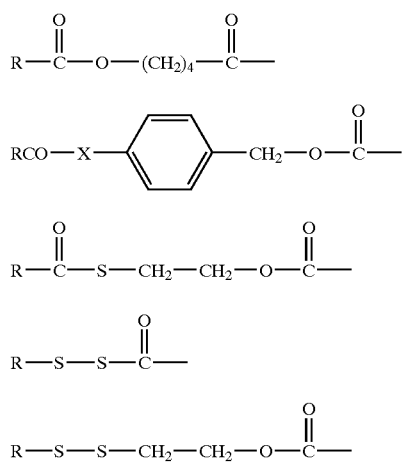

-continued

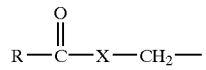

where X is O or S; and wherein R is C1–C18 alkyl, alkenyl, alkynyl, aryl, and aralkyl, straight or branched, and wherein the 5'-OH group may further be modified to form a monoboranophosphate radical, diboranophosphate radical, triboranophosphate radical, stabilized monophosphate radical, stabilized diphosphate radical, or stabilized triphosphate radical.

In another aspect of the invention, there are provided nucleoside analogs and prodrugs of Formula 4, in which the sugar is either in the L- or D-configuration:

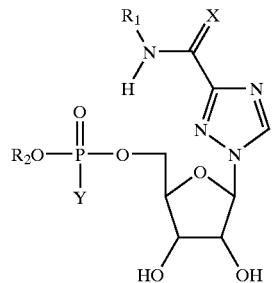

Formula 4 wherein X is O or NH; Y is OR₂ or BH₃; R₁ is H or a masking group of the amino group; and R₂ is a masking group of the phosphate, preferably having any of the following structures:

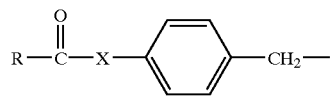
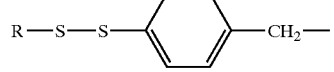
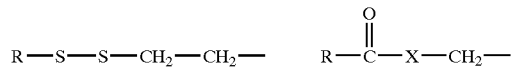

where X is O, or S; and R is C1–C18 alkyl, alkenyl, alkynyl, aryl, aralkyl straight or branched.

In another aspect of the invention, there are provided nucleoside analogs and prodrugs of Formula 5, in which the sugar is either in the L- or D-configuration:

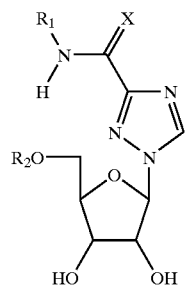

Formula 5 where X is O or NH, R₁ is H or a masking group; R₂ is phosphate group with a masking group having any one of the following structures:

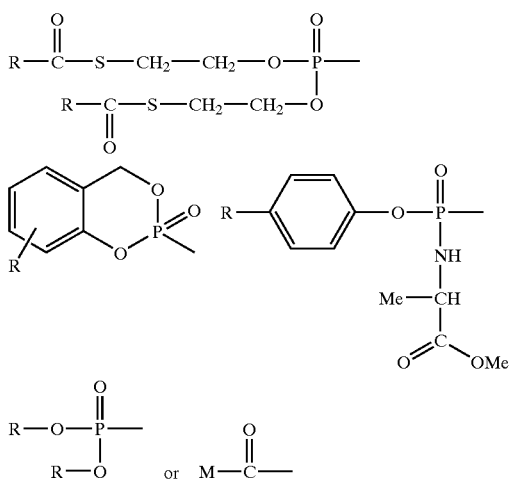

where R is substituted or unsubstituted C1–C18 alkyl, alkenyl, alkynyl, aryl, and aralkyl, (which may be straight or branched), or halogen, and wherein M is selected from alkyl, alkenyl, alkynyl, aralkyl, aryl, and a group of hydrophobic compounds, including cholesterol, vitamin D and various derivatives thereof, and cholic acid derivatives bearing a linker which can be covalently attached to the carbonyl atom of the cholic acid.

In yet another aspect of the invention, there are provided nucleoside analogs and prodrugs of Formula 6:

Formula 6

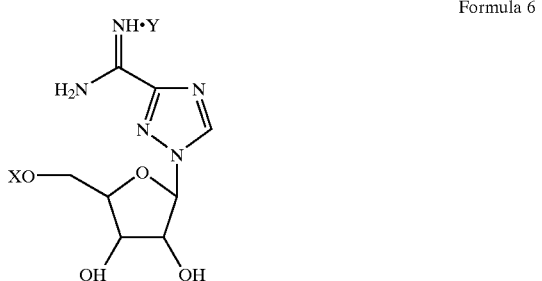

wherein X is a phosphate or boranophosphate, and wherein Y is null or an acid to form a pharmacologically acceptable salt.

In still another aspect of the invention, there are provided nucleoside analogs and prodrugs of Formula 7 in which the sugar may be in D- or L-configuration Formula 7

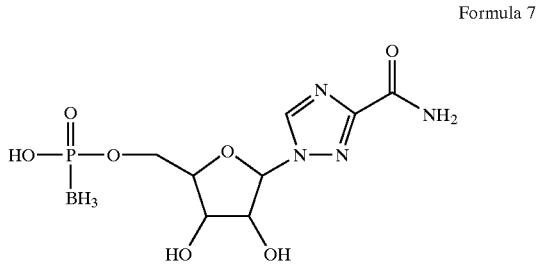

In yet another aspect of the invention, a pharmaceutical composition comprises a therapeutically effective amount of any one or a combination of Formulas 1–7, or a pharmaceutically acceptable ester or salt thereof admixed with at least one pharmaceutically acceptable carrier.

In a further aspect of the invention, a compound according to any one of Formulas 1–7 is used in the treatment of any condition, which responds positively to administration of the compound, and according to any formulation and protocol which achieves the positive response. Among other things, it is contemplated that compounds of Formulas 1–7 may be used to treat an infection, an infestation, a cancer, tumor or other neoplasm, giant cell arteritis, or an autoimmune disease.

BRIEF DESCRIPTION OF THE DRAWINGS

FIG. 1 is a graphical depiction of the effect of Viramidine™ (1.39 $\mu$g/ml), D-Ribavirin (1.22 $\mu$g/ml), and L-Ribavirin (1.22 $\mu$g/ml) on Type 1 cytokine synthesis in SEB-activated human T-cells. The data shown are arithmetic mean and SEM for 7 donors.

FIG. 2 is a graphical depiction of the effect of 0.625–10 $\mu$M Viramidine™ on Type 1 cytokine synthesis in SEB-activated human T-cells. The data represent 4 individual donors.

DETAILED DESCRIPTION

The inventors generally contemplate various nucleoside analogs and prodrugs thereof, and especially those in which the heterocyclic base comprises a 5-membered nitrogen-containing ring. Further especially preferred compounds also include metabolites of such compounds, and particularly those that exhibit biological activity (e.g., antiviral effect, modulation of Th1 Th2 cytokine balance, antineoplastic effect, etc.).

The terms "nucleoside" and "nucleoside analog" are interchangeable and refer to a compound comprising a sugar (e.g., pentose or modified pentose) that is covalently coupled to a heterocycle, or aromatic heterocycle. As also used herein, the term "nucleotide" refers to a nucleoside in which the 5'-hydroxyl group of a nucleoside is esterified with a phosphate, boranophosphate, or otherwise modified phosphate group.

The term "heterocycle" or "heterocyclic base" as used herein refers to a saturated or unsaturated carbocyclic radical having at least one hetero atom (e.g., N, O or S) within the ring, wherein the heterocycle may optionally be substituted (e.g., with one or more of a hydroxy, oxo, amino, imino, lower alkyl, bromo, chloro and/or cyano group).

The term "D-nucleoside" as used herein refers to a nucleoside that has a sugar moiety in D-configuration. Similarly, the term "L-nucleoside" refers to a nucleoside that has a sugar moiety in L-configuration, wherein the terms "L-configuration" and "D-configuration" are used throughout the present invention to describe the stereochemical configuration of the sugar moiety of the nucleoside.

The term "protecting group" refers to a chemical group that is added to an oxygen, nitrogen, or phosphorus atom to prevent its further reaction during the course of derivatization of other moieties in the molecule in which the oxygen, nitrogen, or phosphorus is located. However, it should be recognized that suitable protecting groups may be removed from the oxygen, nitrogen, or phosphorus atom in vivo via an enzymatic or non-enzymatic reaction.

The term "lower alkyl" refers to methyl, ethyl, n-propyl, isopropyl, n-butyl, t-butyl, i-butyl, or n-hexyl. This terrn is further exemplified to a cyclic, branched or straight chain from one to six carbon atoms. Thus, the term "lower alkenyl" refers to a lower alky with at least one double bond, and the term "lower alkynyl" refers to a lower alkyl with at least one triple bond. Where the term "lower" is omitted from the above terms, all of the above hydrocarbons may have more than six carbon atoms. The term "aryl" as used herein refers to an aromatic carbocyclic radical having a single ring (e.g., phenyl) or two condensed rings (e.g., naphthyl), which can optionally be substituted with hydroxyl, lower alky, chloro, and/or cyano.

The terms "immunomodulator" and "modulator" are used interchangeably herein and refer to natural or synthetic products capable of modifying the normal or aberrant immune system through stimulation or suppression. Particularly contemplated stimulations and/or suppressions include stimulation and/or suppression of one or more cytokines, and especially to those belonging to the group of Th1 cytokines and Th1 cytokines.

The compounds of Formulas 1–7 may have multiple asymmetric centers. Accordingly, they may be prepared in either optically active form or as a racemic mixture. The scope of the invention as described and claimed encompasses the individual optical isomers and non-racemic mixtures thereof as well as the racemic forms of the compounds of Formulas 1–7. The term "α" (alpha) and "β" (beta) indicate the specific stereochemical configuration of a substituent at an asymmetric carbon atom in a chemical structure.

"Pharmaceutically acceptable salts" may be any salts derived from inorganic and organic acids or bases, and especially contemplated acids include inorganic acids (e.g., HCl, HBr, etc.) and organic acids (e.g., fumaric acid, maleic acid, etc.)

Contemplated Compounds

It is generally contemplated that compounds according to the inventive subject matter will have a sugar moiety (and most preferably a ribofuranosyl moiety in D- or L-configuration) that is covalently coupled to a heterocyclic base, which is preferably a 5-membered ring with nitrogen as heteroatom, and most preferably a 1,2,4-triazole.

Therefore, in one aspect of the inventive subject matter, contemplated compounds may generally fall within the scope of Formula 1, wherein the sugar is in the L- or D-configuration:

Formula 1

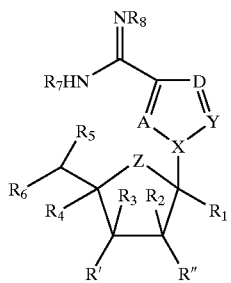

and wherein A, X, Y, and D are independently selected from N or C—$R_9$; $R_9$ is independently H, halogen, lower alkyl, alkenyl, alkynyl, amino, CN, SH, CHO, COOH, $CH_2OH$, or hydroxyl; Z is O, $CH_2$ or S; R' and R" are independently selected from H, hydroxyl, protected hydroxyl, or halogen; $R_1$, $R_2$, $R_3$, $R_4$, and $R_5$, are independently selected from H, halogens, CN, $CH_2OH$, lower alkyl, vinyl or acetylene; when $R_2$ is hydroxyl, then, R" that is attached to the same carbon as that of $R_2$ is not halogen; when $R_3$ is hydroxyl, then, R' that is attached to the same carbon as that of $R_3$ is not halogen; $R_6$ is independently selected from H, hydroxyl, protected hydroxyl, —$CH_2OH$, —$CH_2PO(OH)_2$—, O-amino acids, O-retinoic acid, O-cholesteral, O-cholic acid, O-coumarinic acid, O-salicylic acid, O-succinic acid, O-bile acid, O-lipids, O—P(O)—(O—$CH_2$—$CH_2$—S—CO—$CH_3$)$_2$; O-steroids; boranophosphate, boranophosphate derivatives, O-monophosphate derivatives, O-diphosphate derivatives or O-triphosphate derivatives; $R_7$ is independently selected from H, alkyl, $CH_3COO$—, $CH_3COO$-Phenyl-$CH_2$—O—CO—, phenyl, —$(CH_2)$n-COOH, coumarinic acid, salicylic acid, dithiosuccinoyl derivatives, reductase mediated cleavable groups, phosphonoformic acid or phosphoramidates groups; $R_8$ is independently selected from H, H*HCl, H*HBr, lower alkyl, phenyl, $CH_3COO$—, $CH_3COO$-Phenyl-$CH_2$—O—CO—, phenyl, or —$(CH_2)$n-COOH; $R_7$ and $R_8$ may form a cyclic structure or be independently an amino acid.

However, particularly preferred compounds according to another aspect of the inventive subject matter will include a triazole heterocyclic base and may have a structure according to Formula 2, in which the sugar is either in the L- or D-configuration:

Formula 2

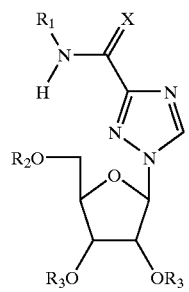

wherein X is O, NH; $R_1$ is H or a masking group of the amino group; $R_2$ is selected from H, boranophosphate, boranophosphate derivative, R'—C(O)—, wherein R' is substituted or unsubstituted alkyl, substituted or unsubstituted alkenyl, substituted or unsubstituted alkynyl, or $R_2$ is a protected or unprotected monophosphate, diphosphate, or triphosphate, and $R_3$ is independently H or C1–C18 acyl. The term "boranophosphate derivative" as used herein refers to a group of the formula —P(X)(BH$_3$)OY, wherein X is O or S, and wherein Y is a group that forms an ester with the phosphate (e.g., substituted or unsubstituted acyl, or SATE). Thus, the term "boranophosphate" as used herein refers to a group having the structure —O—P(O)(BH$_3$)OH or —P(O)(BH$_3$)OH.

In yet another aspect of the invention, nucleoside analogs will have a structure according to Formula 3, in which the sugar is either in the L- or D-configuration:

Formula 3

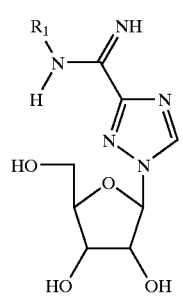

wherein $R_1$ is a masking group having any of the following structures:

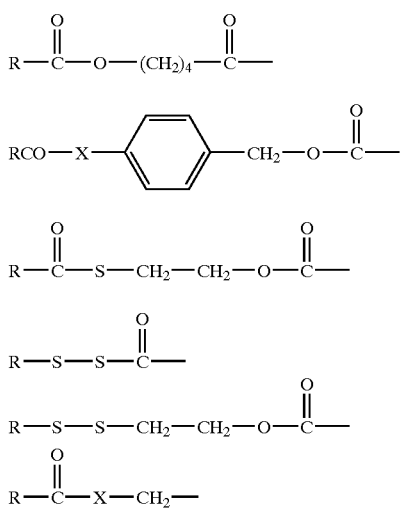

where X is O or S; and wherein R is C1–C18 alkyl, alkenyl, alkynyl, aryl, and aralkyl, straight or branched. The 5'OH group of such compounds may further be modified to form a monoboranophosphate radical, diboranophosphate radical, triboranophosphate radical, stabilized monophosphate radical, stabilized diphosphate radical, or stabilized triphosphate radical.

In a further aspect of the invention, nucleoside analogs will have a structure according to Formula 4, in which the sugar is either in the L- or D-configuration:

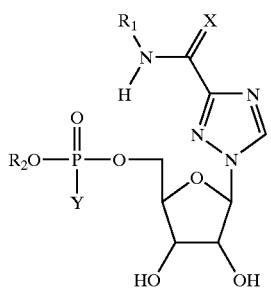

Formula 4 wherein X is O or NH; Y is $OR_2$ or $BH_3$; $R_1$ is H or a masking group of the amino group; and $R_2$ is a masking group of the phosphate, preferably having any of the following structures:

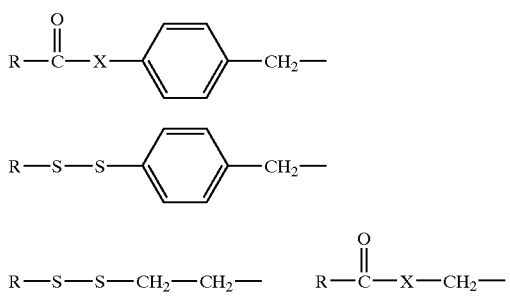

in which X is O, or S; and R is C1–C18 alkyl, alkenyl, alkynyl, aryl, aralkyl straight or branched.

In yet another aspect of the invention, nucleoside analogs will have a structure according to Formula 5, in which the sugar is either in the L- or D-configuration

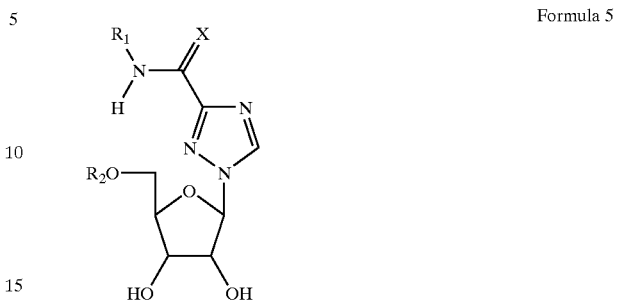

Formula 5 where X is O or NH, $R_1$ is H or a masking group; $R_2$ is phosphate group with a masking group having any one of the following structures:

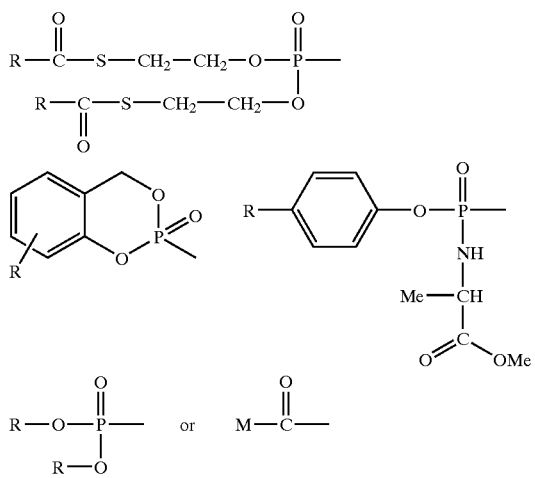

where R is substituted or unsubstituted C1–C18 alkyl, alkenyl, alkynyl, aryl, and aralkyl, (which may be straight or branched), or halogen, and wherein M is selected from alkyl, alkenyl, alkynyl, aralkyl, aryl, and a group of hydrophobic compounds, including cholesterol, vitamin D and various derivatives thereof, and cholic acid derivatives bearing a linker which can be covalently attached to the carbonyl atom of the cholic acid.

In a still further aspect of the invention, nucleoside analogs will have a structure of Formula 6

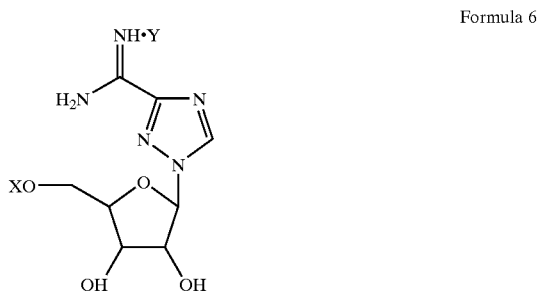

Formula 6 wherein X is a phosphate or boranophosphate, and wherein Y is null or an acid to form a pharmacologically acceptable salt.

In another aspect of the invention, there are provided nucleoside analogs and prodrugs of Formula 7 in which the sugar may be in D- or L-configuration Formula 7

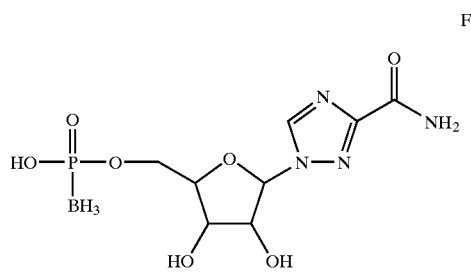

Where boranophosphates are employed in contemplated compounds, it should be recognized that such boranophosphates may be designated in various manners. For example, where the sugar has an O radical to which the boranophosphate is coupled, the boranophosphate will be designated as —P(O)(BH$_3$)OH, or —P(O)(BH$_3$)O$^{31}$. On the other hand, where the sugar has a C radical to which the boranophosphate is coupled, the boranophosphate will be designated as —O—P(O)(BH$_3$)OH, —O—P(O)(BH$_3$)O$^-$. Moreover, it should be appreciated that the boranophosphate may be further coupled to at least one of a phosphate group and/or another boranophosphate to form a modified di-, tri-, or polyphosphate.

Similarly, contemplated boranophosphates may also be further modified to form a boranophosphate derivative. For example, contemplated boranophosphate derivatives include esters with acids (e.g., amino acids, alkylcarboxylic acids, etc.), or from a peptide and/or amide bond with a primary or secondary amine. Particularly preferred boranophosphate derivatives will include those in which the modification to the boranophosphate group is removed under phgsyiological conditions (and most preferably in a particular cellular environment and/or organ). Use of boranophosphate modified nucleosides/nucleotides and their prodrugs may be especially advantageous as such compounds will exhibit increased resistance to phosphatases that would otherwise remove the phosphate group from a nucleotide. Thus, contemplated boranophosphate nucleosides/nucleotides will be stabilized in a cell or other in vivo environment. Moreover, it should be recognized that where the nucleotide form of a contemplated compound is the active form, boranophosphate nucleosides/nucleotides may be administered for treatment in an active form and thus no more activation by an intracellular kinase is required.

Still further, stabilized nucleotides may also be prepared from nucleoside phosphates in which the phosphate group is protected with a cyclic structure that is preferentially cleaved in a target cell or target organ. Especially preferred stabilized nucleotides with a cyclic structure may be prepared as described by Erion et al. in U.S. Pat. No. 6,312,622, which is incorporated by reference herein. Alternatively, contemplated nucleotides may also be stabilized using SATE (S-acyl-2-thioethyl), and the preparation of SATE protected nucleotides is well known in the art (e.g., Tosquellas, G. et al. in Nucleic Acids Res. (1998), 26, 2069, incorporated by reference herein).

While contemplated compounds may be prepared in vitro using combinatorial and/or conventional synthetic approaches, it should be especially recognized that contemplated compounds according to Formulae 1–7 also include their metabolites formed inside or outside of a cell in vitro or in vivo, and wherein the metabolite may be formed in an enzymatic reaction or a non-enzymatic reaction.

For example, where the metabolite is formed in an enzymatic reaction in which the molecular weight of the compound increases, contemplated enzymes include kinases (e.g., formation of a mono-, di-, or triphosphate from contemplated compounds), transferases (e.g., terminal nucleotidyl transferase adds a polynucleotide to the compound), or polymerases (e.g., DNA-dependent RNA polymerase adds a polyribonucleotide to the compound). Similarly, where the reaction is a non-enzymatic reaction, the molecular weight of contemplated compounds may be increased via thiol oxidation to form the corresponding disulfide (e.g., where contemplated compounds include an SH group). In another example, the metabolite may be formed in an enzymatic reaction in which the molecular weight of the compound decreases, and contemplated enzymes include aminohydrolases (e.g., deprotection of a protected amino group), phosphatases (removal of a phosphate group from a mono-, di-, or triphosphate), nucleosidases (e.g., hydrolytic cleavage of the heterocyclic base from the sugar), and so on.

Especially contemplated metabolites will include active metabolites, wherein the term "active metabolite" as used herein refers to any metabolite of contemplated compounds that exhibits biological activity (e.g., antiviral activity, immunomodulatory activity, antineoplastic activity, etc.). It should be recognized that biological activity may be readily determined in an assay in which the metabolite is formed in sufficient quantity (e.g., in human, animals, or cell culture) after administration of contemplated compounds to the assay.

Contemplated Synthesis

There are numerous methods and synthetic routes available to a person of ordinary skill in the art to produce some, if not all of the contemplated compounds, and the following examples provide for exemplary guidance.

For example, prodrug forms of Viramidine™, Ribavirin, Levovirin, or other contemplated nucleosides according to the inventive subject matter may be prepared via acetylation, and Scheme 1 below depicts synthesis of a tri-O-acetyl derivative of Viramidine™.

Scheme 1

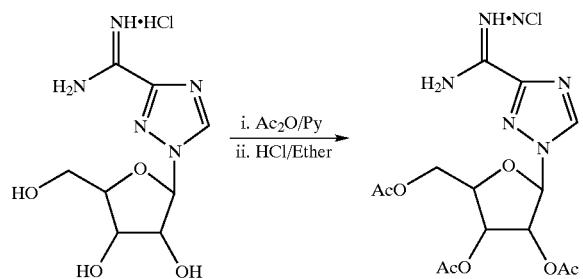

Similarly, 5'-Retinoyl derivatives (or other acid esters) of contemplated compounds may be prepared as depicted in Scheme 2 below

Scheme 2

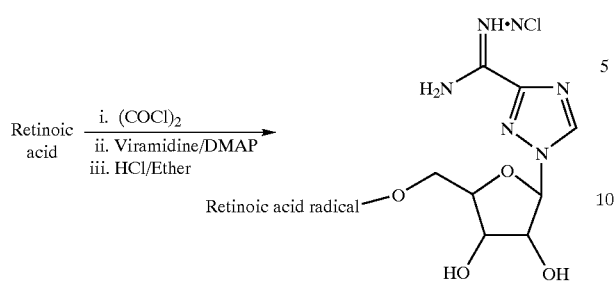

Other 5'-derivatives of Viramidine™ include synthetic routes as shown in Schemes 3–6. Most of the compounds in these schemes may be obtained following protocols similar to those previously described (see e.g., C. Sergheraert, C. Pierlot, A. Tartar, Y. Henin, M. Lemaitre, *J. Med. Chem.*, 36, 826–830, 1993).

Scheme 3

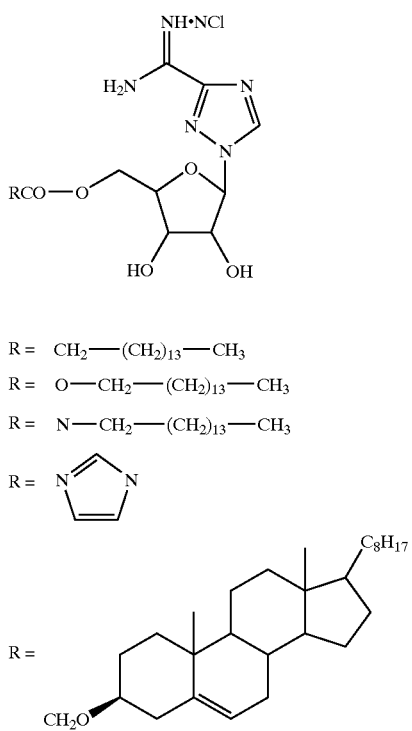

Other groups for R include bile acids, lipids, cholic acid, cholesterol derivatives, and vitamins. Synthesis of salicylic-based prodrugs of Viramidine™ may be obtained as follows:

Scheme 4

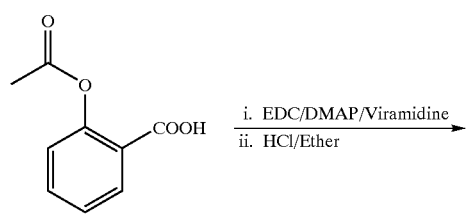

-continued

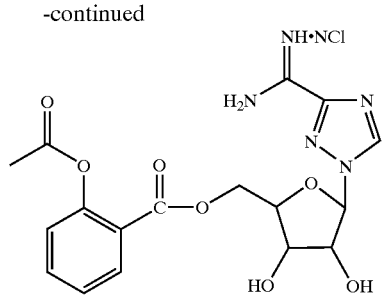

Amino acid esters are considered yet another class of prodrugs and can be synthesized as shown below:

Scheme 5

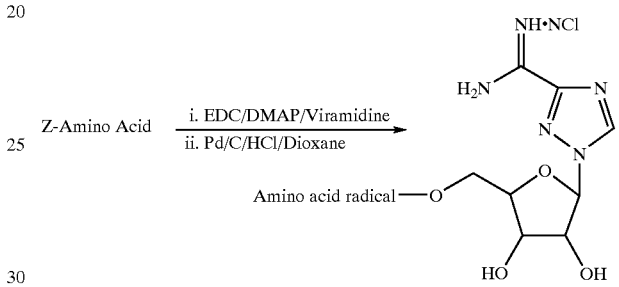

For specific delivery of drugs to the liver and the biliary system the endogenous bile acid transport system is an attractive candidate. Synthesis of bile acid conjugates of Viramidine™ could be accomplished as represented below:

Scheme 6

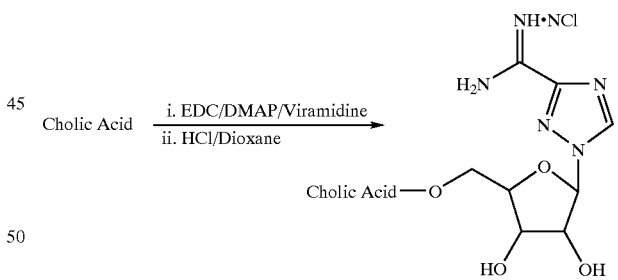

Nucleotide derivatives may be prepared as shown in exemplary Scheme 7. Protecting the negative charges of phosphates with neutral substituents would form more lipophilic derivatives, which is expected to revert back to the corresponding monophosphates once inside a living cell.

Scheme 7

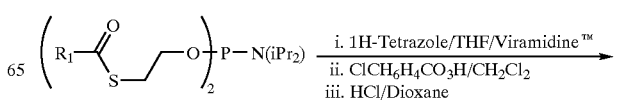

-continued

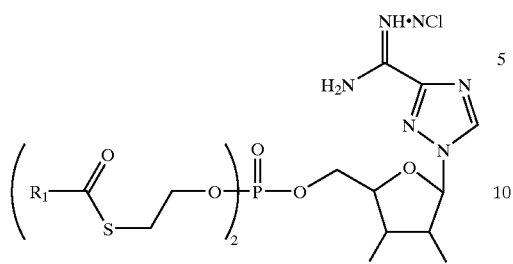

in which $R_1$ is an alkyl group, including $CH_3C(O)S$—$CH_2CH_2$—; $(CH_3)_2CHC(O)S$—$CH_2CH_2$; $(CH_3)_3CC(O)S$—$CH_2CH_2$—; $(CH_3)_3CC(O)OCH_2$—; $C_6H_5C(O)S$—$CH_2CH_2$— or $HOCH_2CH_2SS$—, and $CH_2CH_2$—.

Amino acid phosphoramidates are yet another class of prodrugs that may be synthesized as described below in Scheme 8A:

Scheme 8A

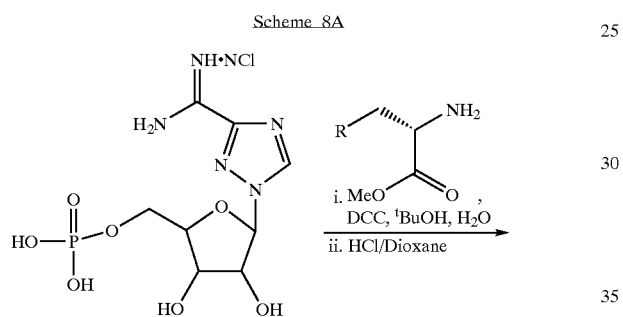

R = Anything Except Hydrogen

Still further contemplated monophosphate prodrugs of Viramidine™ are shown below in Scheme 8B:

Scheme 8B

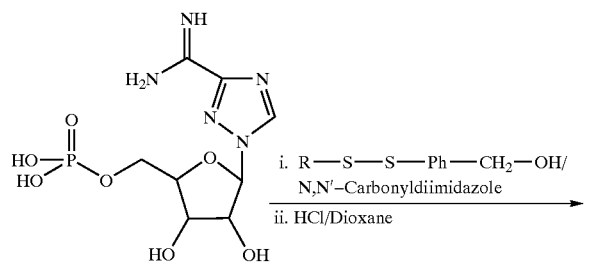

-continued

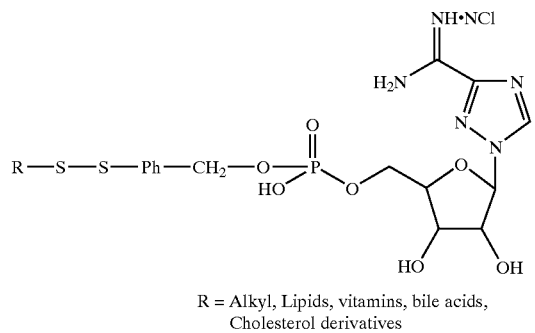

R = Alkyl, Lipids, vitamins, bile acids, Cholesterol derivatives

Salicylate-based nucleotide prodrugs of Viramidine™ may be obtained by the following exemplary Scheme 9:

Scheme 9

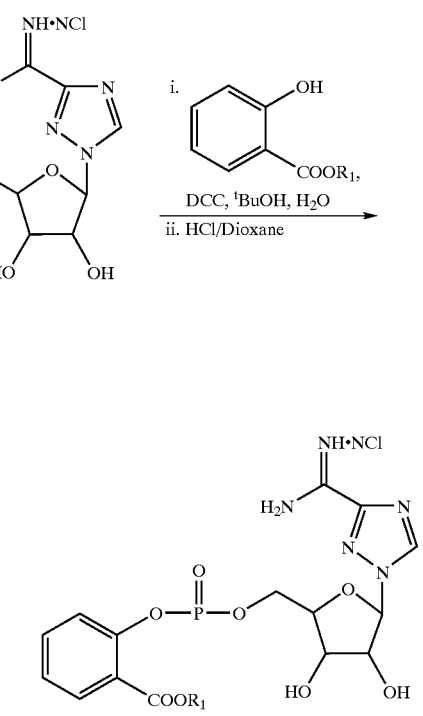

$R_1 = CH_3$
$R_1 = Ph$
$R_1 = H$ $R_1 = $ 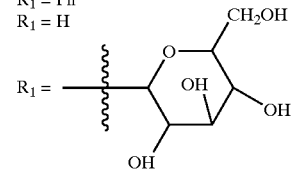

Prodrugs of nucleoside 5'-di- or triphosphates provide an attractive alternative since they would likely bypass one or more metabolic steps. Following are potential nucleotide lipophilic prodrugs, which may be prepared as depicted in Scheme 10 below:

Scheme 10
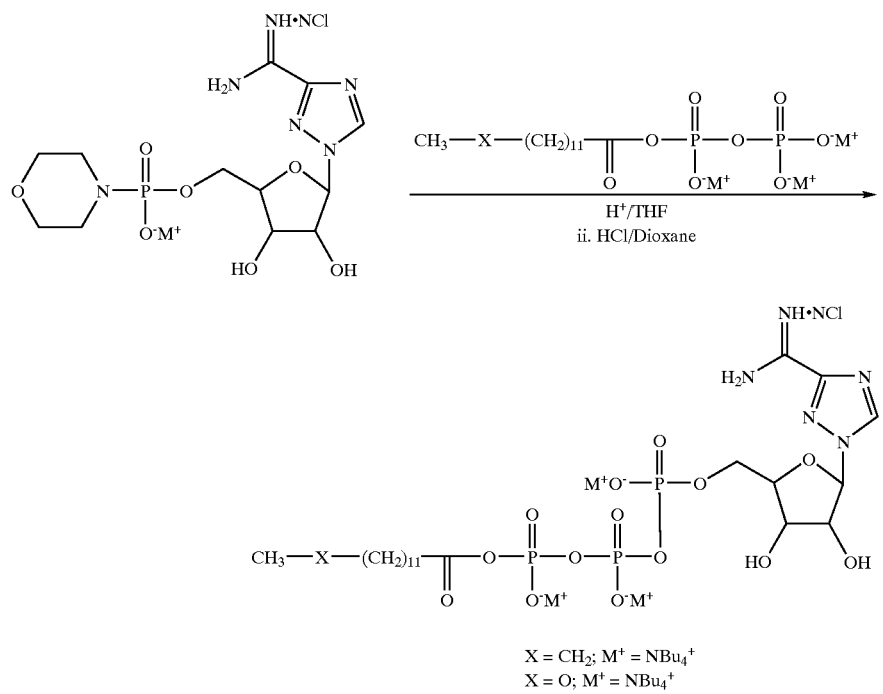
Alternatively, phosphonate prodrugs of Viramidine™ may be prepared following the exemplary Schemes 11 and 12:
Scheme 11
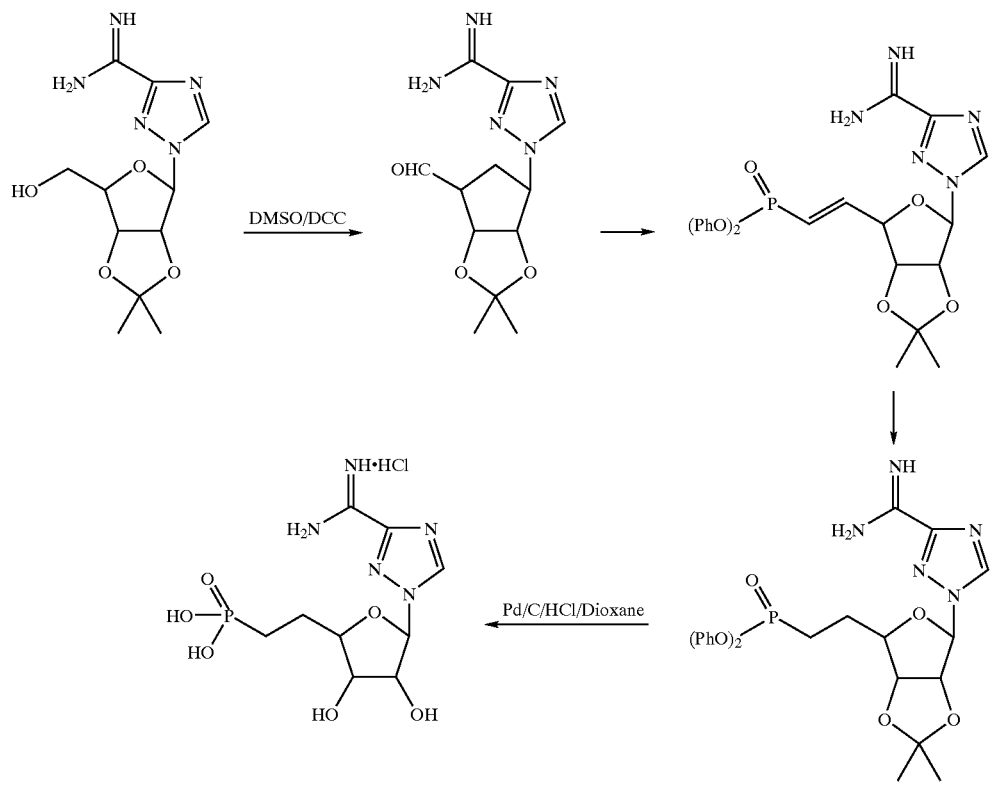

Scheme 12

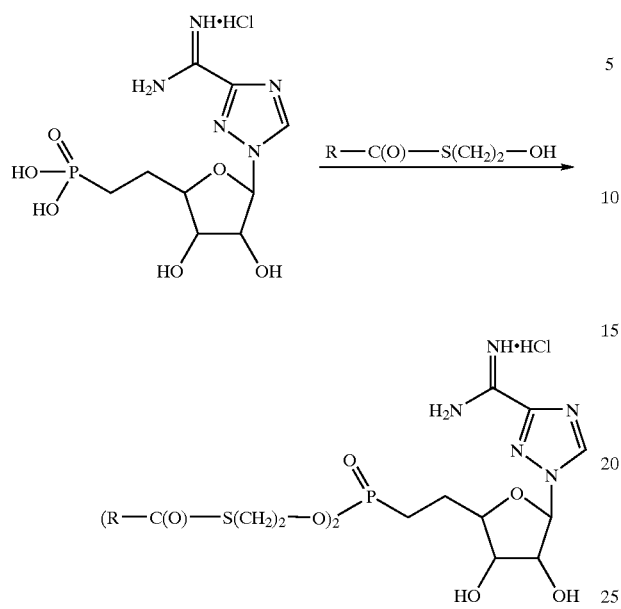

Still further possible prodrugs include the possible combinations of the groups shown in PCT patent application WO 98/39342, WO 98/39343, WO 98/39344 and WO 99/45016, each of which are incorporated by reference herein.

Other contemplated prodrug formations include coumarin-based prodrugs, salicylate based prodrugs, dithiosuccinoyl (Dts)-based prodrugs, reductase mediated prodrugs, 4-acyloxybenzyloxycarbonyl-based prodrugs, rasfamesyl protein transferase prodrugs, succinic acid based prodrugs, and homoserine-based prodrugs, which may be prepared as shown in Scheme 13 below:

Scheme 13

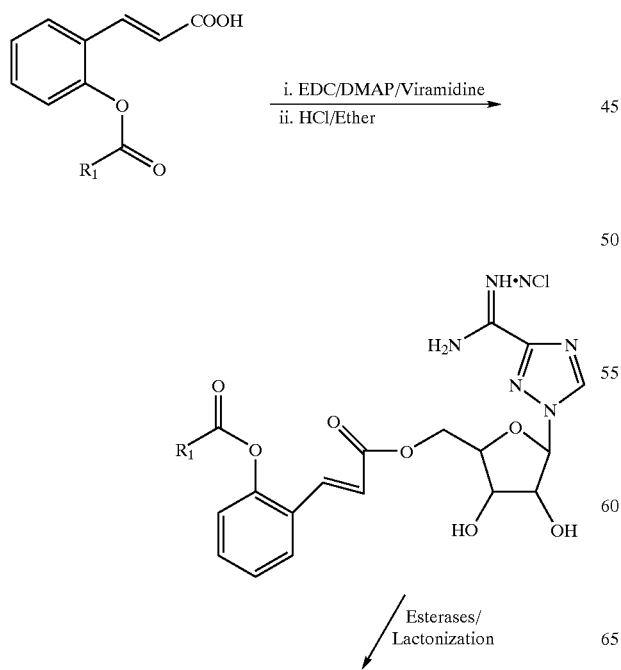

The same coumarinic acid may also be used to mask the amidine functionality of Viramidine™ to produce prodrugs as below. Coumarin based prodrugs are easily cleaved by esterases followed by lactonization, which releases the parent nucleoside to the target site and is shown in the Scheme 13. $R_1$ is independently $CH_3$, fatty acids, cholesterol, cholic acids, bile acids.

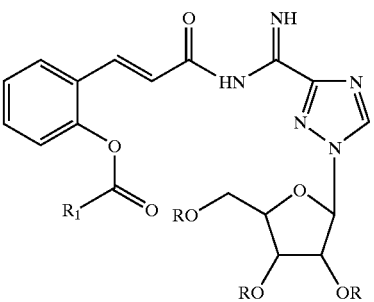

In yet further preferred aspects of the inventive subject matter, it is contemplated that salicylate based prodrugs may exhibit a neighboring group catalysis mechanism. Both hydroxyl and amidine masked salicylates are shown below, and exemplary synthesis may follow Scheme 13 (see above) by substituting salicylic acid for coumarinic acid. $R_1$ is independently $CH_3$, fatty acids, cholesterol, cholic acids, and bile acids.

Dithiosuccinoyl (Dts)-based prodrugs may be particularly advantageous where it is desired that the prodrug gives back the nucleoside via enzyme-activated cleavage.

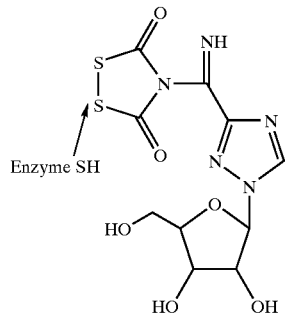

Similarly, reductase-mediated prodrugs are cleaved by a combination of esterases and reductases to give back the nucleoside. Exemplary prodrugs for such mechanism are represented below, wherein $R_1$ is $CH_3$, fatty acids, cholesterol, cholic acids, or a bile acid.

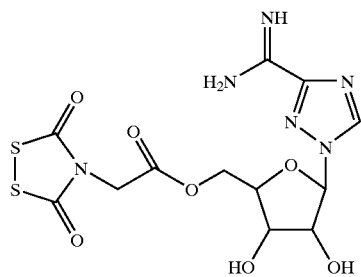

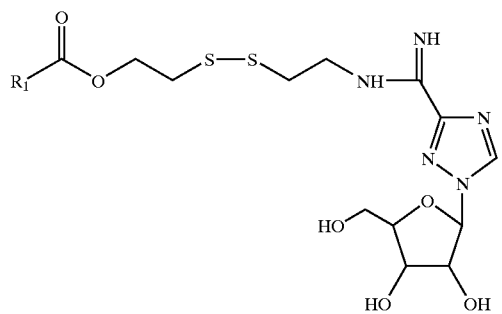

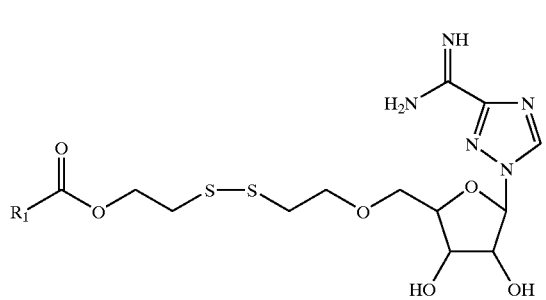

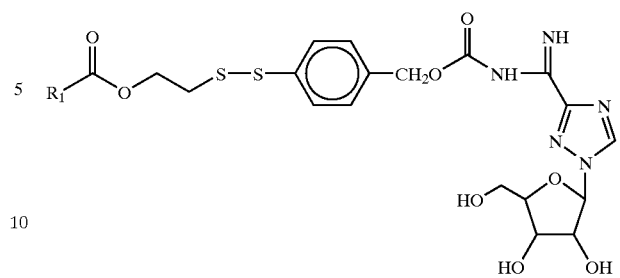

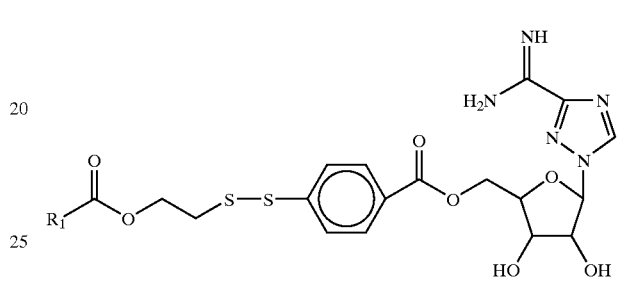

4-Acyloxybenzyloxycarbonyl-based prodrugs may be prepared by using the protecting group strategy used to block the amino group of any amino acids and is represented in Scheme 14. These prodrugs are cleaved by esterases giving back the free nucleoside. $R_1$ is independently $CH_3$, fatty acids, cholesterol, cholic acids, and bile acids.

Scheme 14

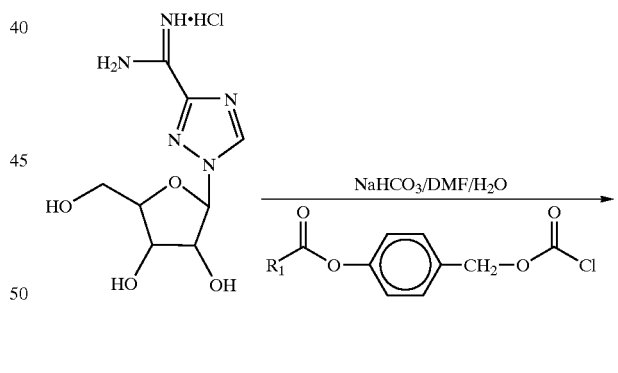

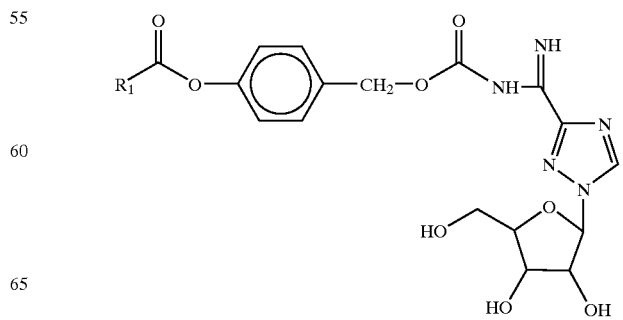

In still further contemplated aspects, the Ras-Farnesyl protein transferase enzyme may be employed to activate prodrugs as depicted below:

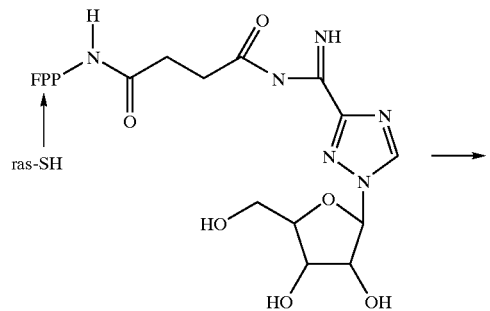

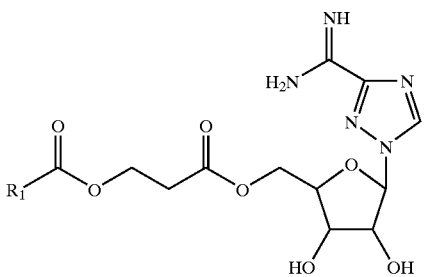

Homoserine-based prodrugs are yet another class of contemplated prodrugs and are depicted below, wherein $R_1$ is independently $CH_3$, fatty acids, cholesterol, cholic acids, and bile acids.

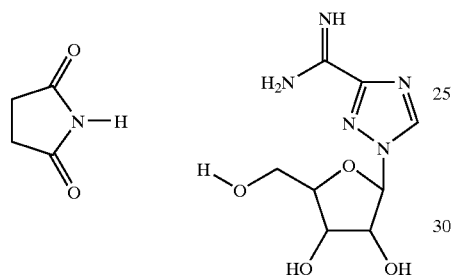

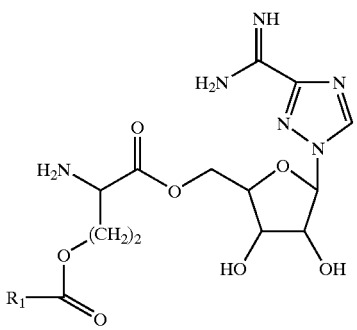

Succinic acid based prodrugs are represented by the following structure. $R_1$ is independently $CH_3$, fatty acids, cholesterol, cholic acids, and bile acids.

Besides the above shown prodrugs for triazole nucleoside analogs, the following types of prodrugs are also contemplated, and a representative example in each group is shown below, in which $R_1$ is independently $CH_3$, fatty acids, cholesterol, cholic acids, and bile acids.

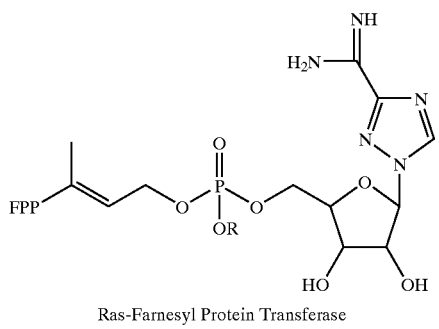

Ras-Farnesyl Protein Transferase

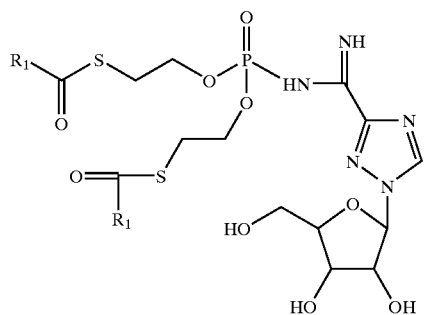

Phosphoramidate-Based

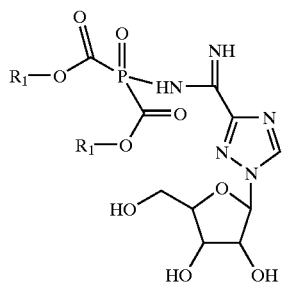

Phosphonoformic acid-Based

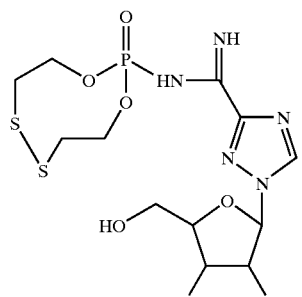

Phosphoramidate-Based

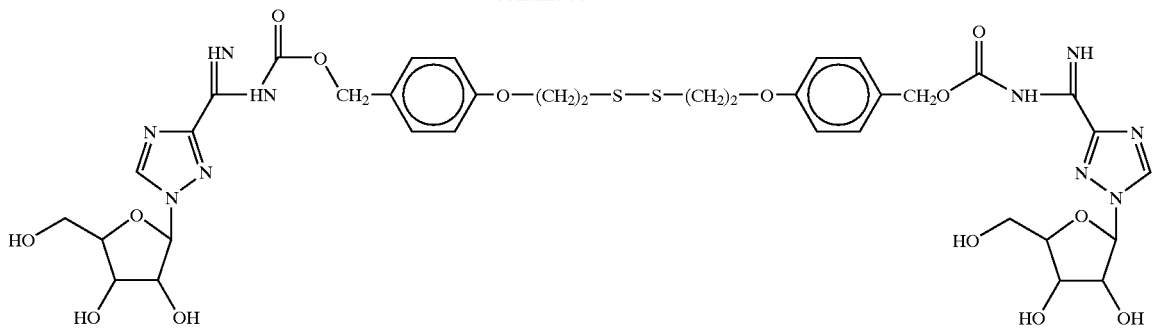

Dimers

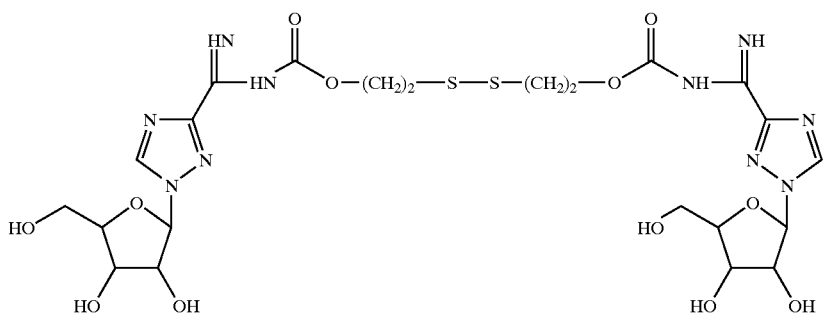

Dimers

Prodrugs of Viramidine™ (and other triazole nucleosides) may also be obtained not only by modifying the sugar portion but also by derivatizing the amidine functionality. Following are a few classes of prodrugs that may be prepared by modifying the amidine group as depicted in Schemes 15 and 16:

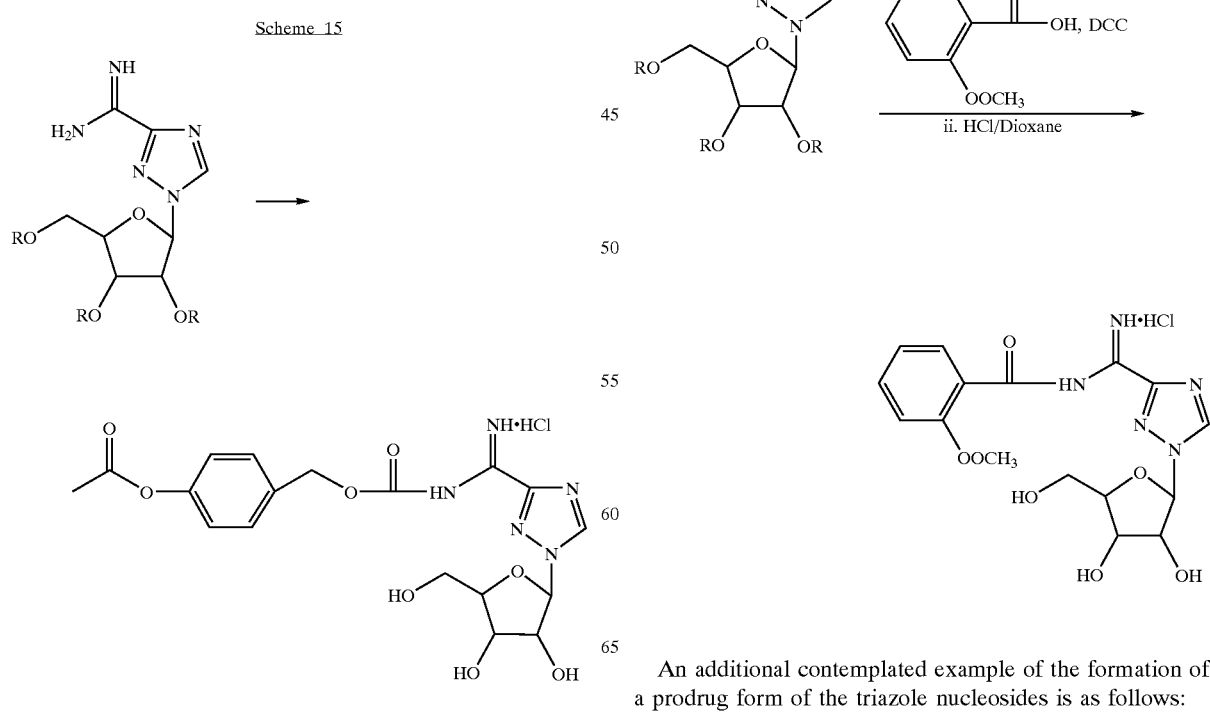

An additional contemplated example of the formation of a prodrug form of the triazole nucleosides is as follows:

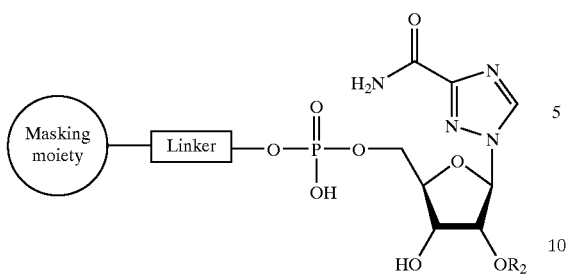

In the above example, the Linker can comprise ligands such as lipids, alkyl groups, bile acid, and vitamins. The Masking Moiety is designed to comprise a masking group that is covalently linked to the Linker.

Examples of the above generalized formula are shown in Schemes 17–23 below:

Scheme 17

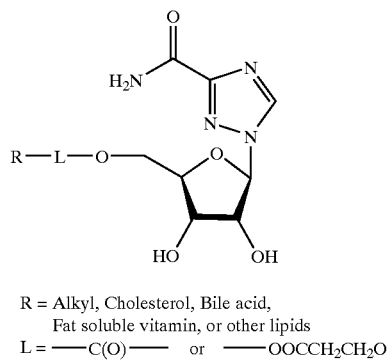

R = Alkyl, Cholesterol, Bile acid,
Fat soluble vitamin, or other lipids
L = —C(O)—   or   —OOCCH$_2$CH$_2$O

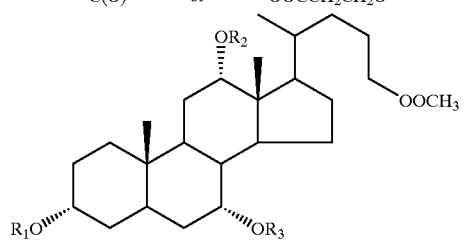

R1 = R2 = R3 = H or Ac
Derivatives of cholic acid

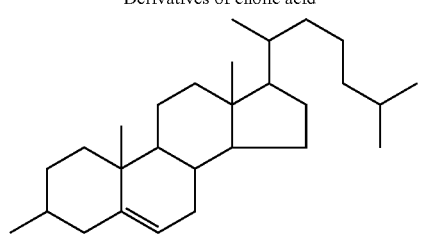

Cholesterol derivative

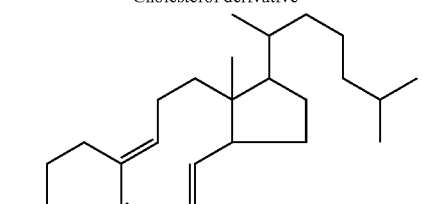

Vitamin D derivative

Scheme 18

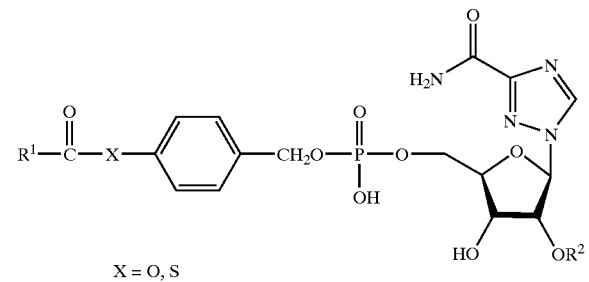

X = O, S
R$^2$ = H, Ac
R1 = Alkyl, lipids, bile acids, fat soluble vitamin, etc.

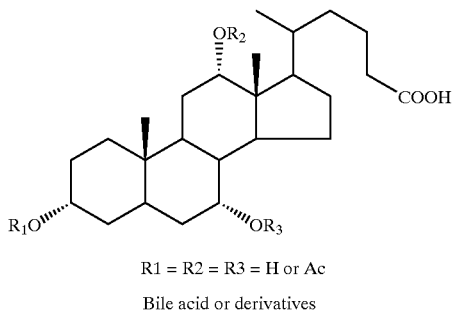

R1 = R2 = R3 = H or Ac
Bile acid or derivatives

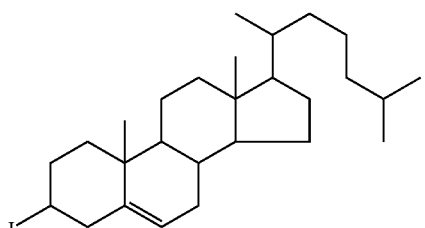

Cholesterol derivative

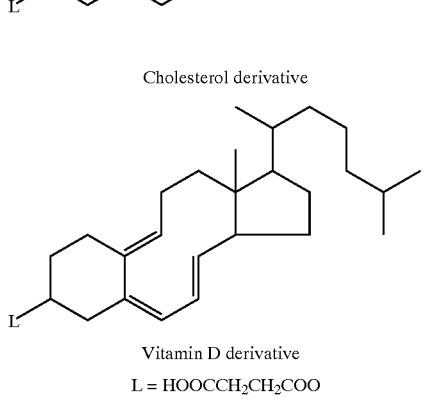

Vitamin D derivative
L = HOOCCH$_2$CH$_2$COO

Scheme 19

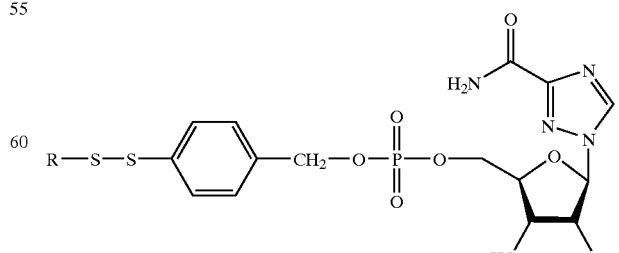

R = Alkyl, Cholesterol, Bile acid, Fat soluble vitamin, or other lipids

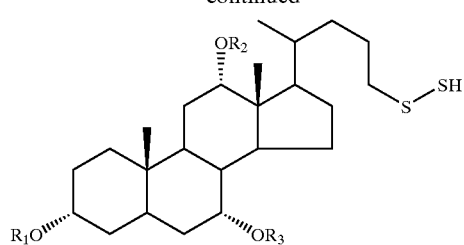
R1 = R2 = R3 = H or Ac
Derivatives of cholic acid
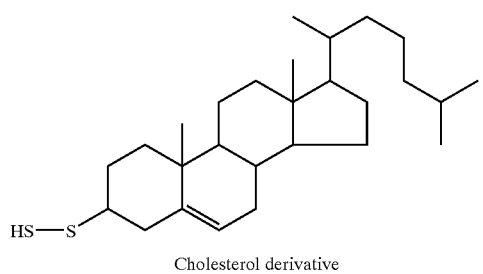
Cholesterol derivative
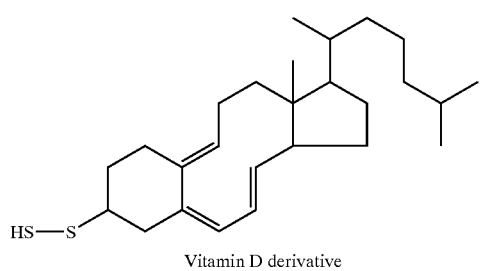
Vitamin D derivative
Scheme 20
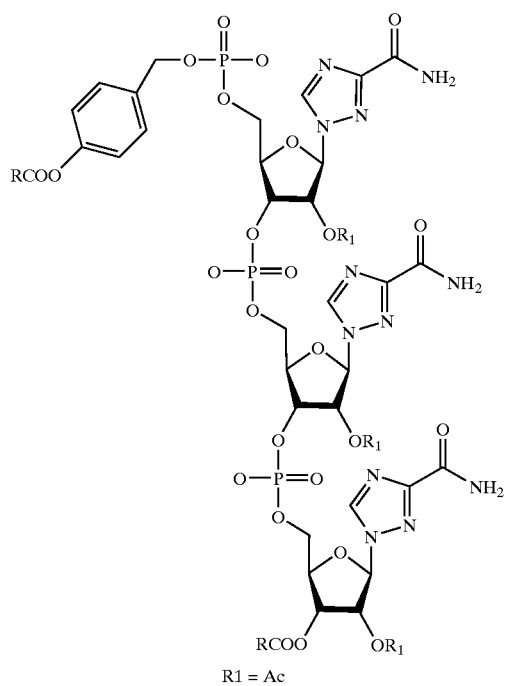
R1 = Ac
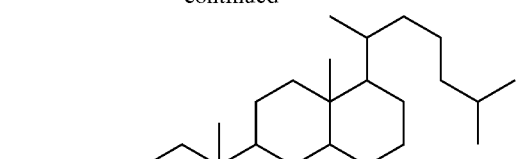
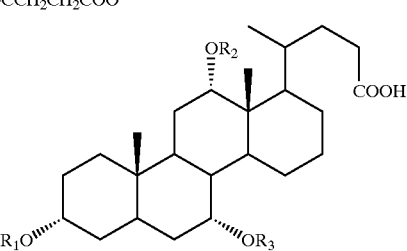
Derivatives of cholic acid
R1 = R2 = R3 = H
R1 = R2 = R3 = Ac
R1 = H, R2 = Ac, R3 = Ac
R1 = Ac R2 = H, R3 = Ac
R1 = R2 = Ac, R3 = H
Scheme 21
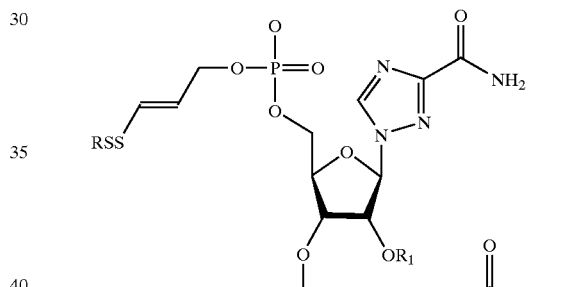
R1 = Ac
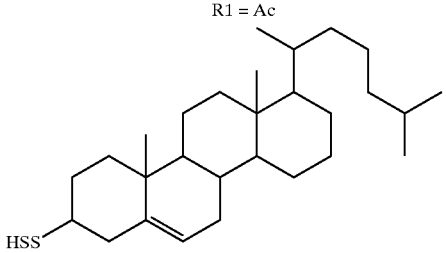

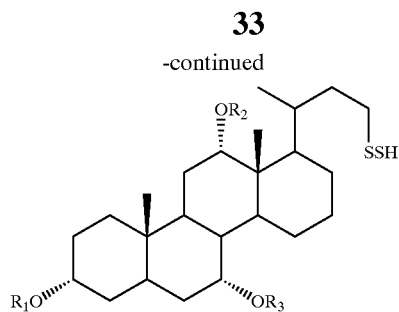

Derivatives of cholic acid

R1 = R2 = R3 = H
R1 = R2 = R3 = Ac
R1 = H, R2 = Ac, R3 = Ac
R1 = Ac R2 = H, R3 = Ac
R1 = R2 = Ac, R3 = H

Scheme 22

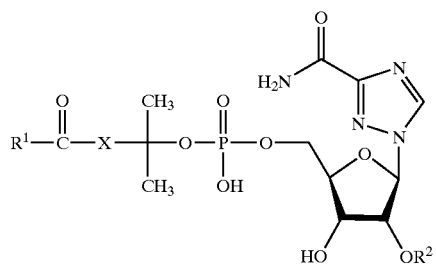

X = O, S
$R^2$ = H, Ac
R = Alkyl, lipids, bile acids, fat soluble vitamin, etc.

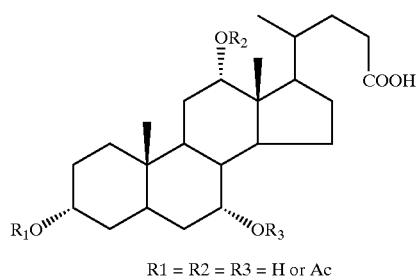

R1 = R2 = R3 = H or Ac

Bile acid or derivatives

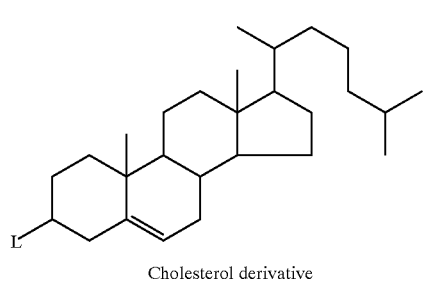

Cholesterol derivative

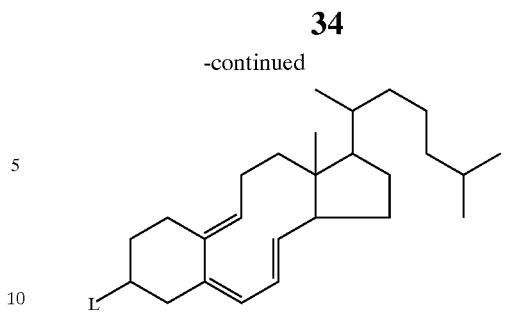

Vitamin D derivative

L = HOOCCH$_2$CH$_2$COO

Scheme 23

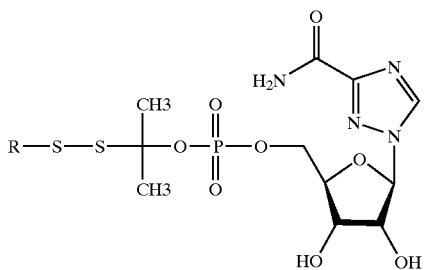

R = Alkyl, Cholesterol, Bile acid, Fat soluble vitamin, or other lipids

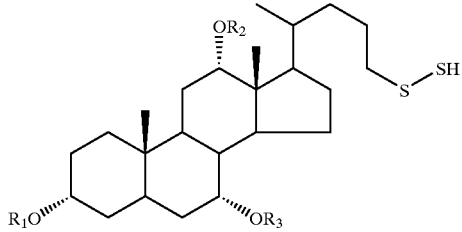

R1 = R2 = R3 = H or Ac

Derivatives of cholic acid

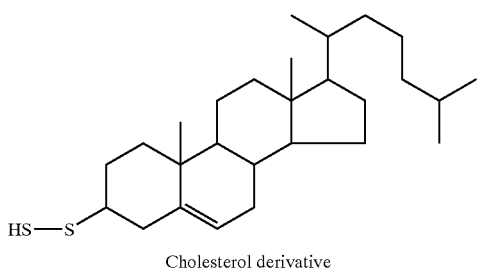

Cholesterol derivative

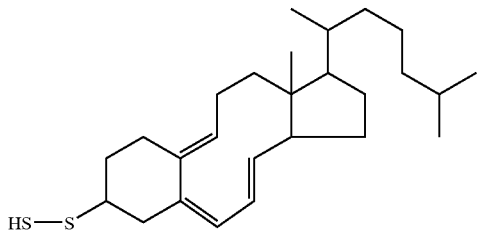

Vitamin D derivative

It is still further contemplated that biotransformations may be applied to various nucleoside analogs (and especially triazole nucleoside analogs), and exemplary schemes are provided in Schemes 24–28 below:

Scheme 24
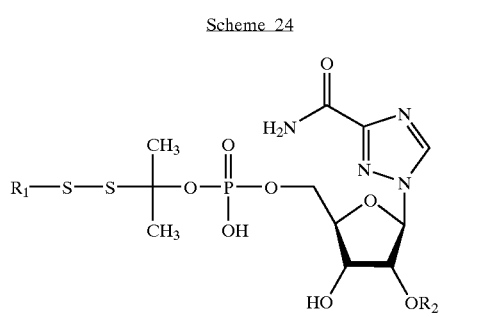
R1 = Lipids, Alkyl, Bile acid,
R2 = H, Ac
↓ Glutathione
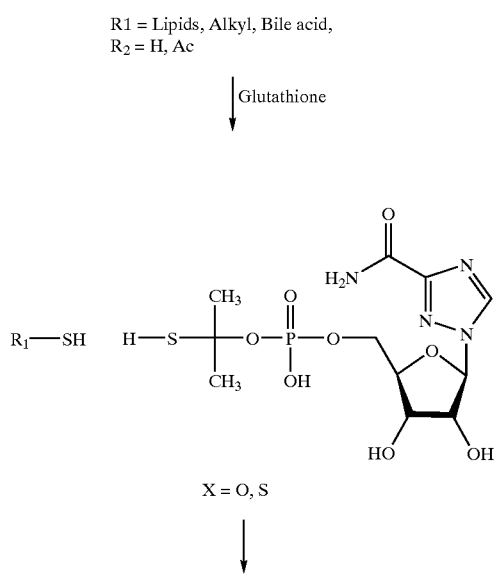
X = O, S
↓
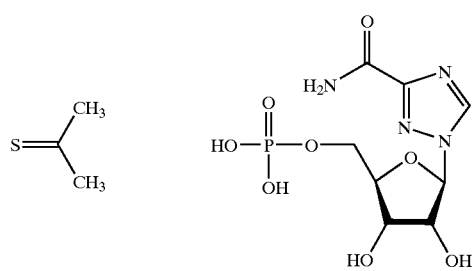
Scheme 25
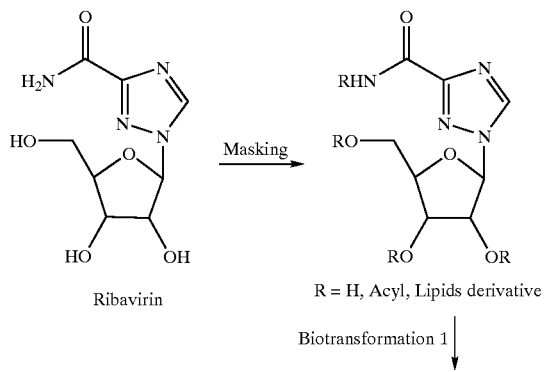
Ribavirin → R = H, Acyl, Lipids derivative
Biotransformation 1 ↓
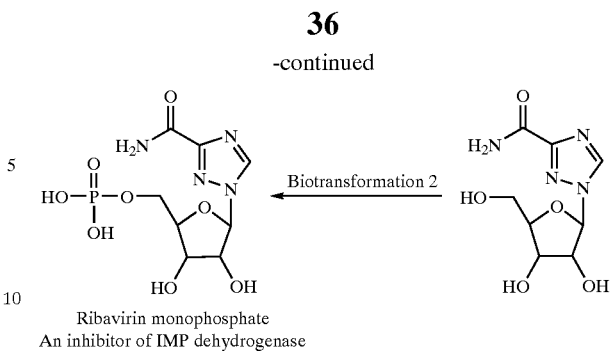
Ribavirin monophosphate
An inhibitor of IMP dehydrogenase
Scheme 26
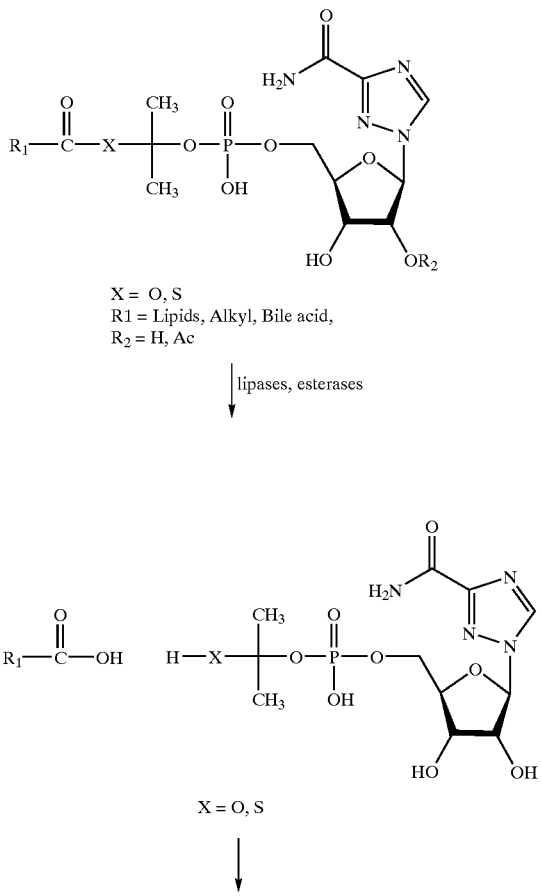
X = O, S
R1 = Lipids, Alkyl, Bile acid,
R2 = H, Ac
↓ lipases, esterases
↓
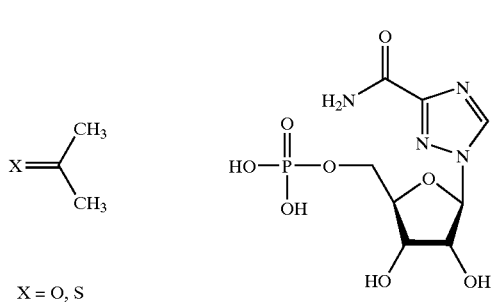
X = O, S

Scheme 27

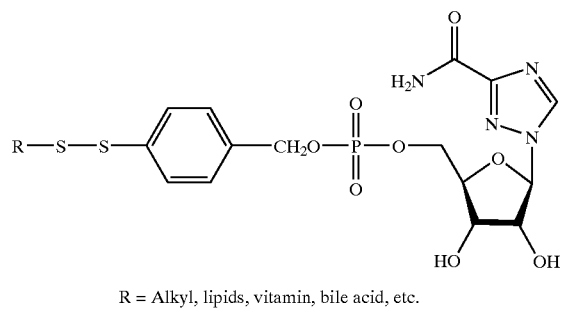

R = Alkyl, lipids, vitamin, bile acid, etc.

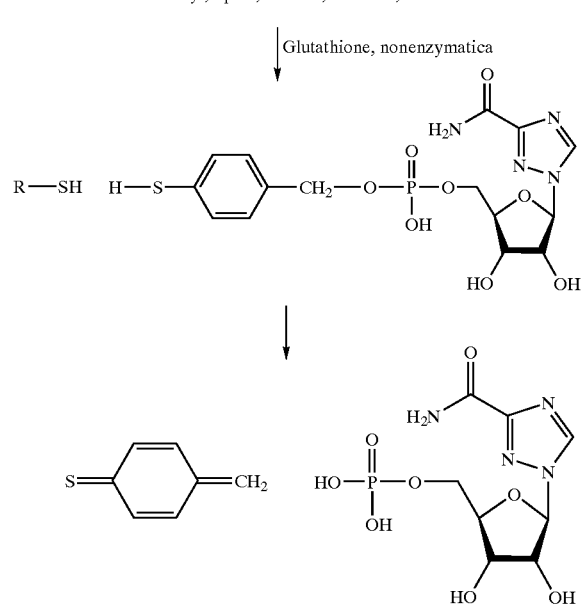

Scheme 28

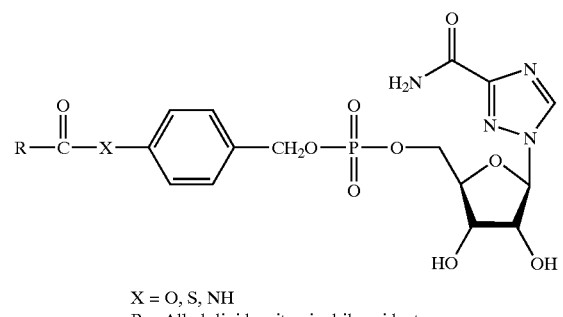

X = O, S, NH
R = Alkyl, lipids, vitamin, bile acid, etc.

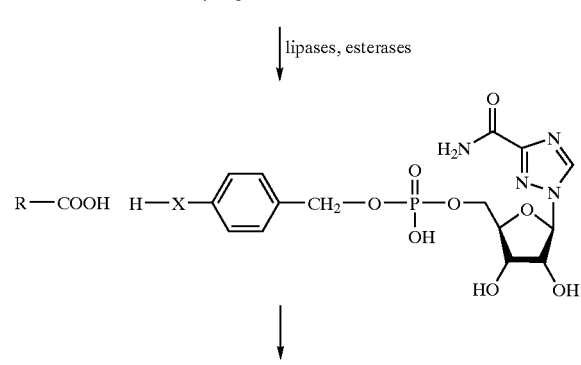

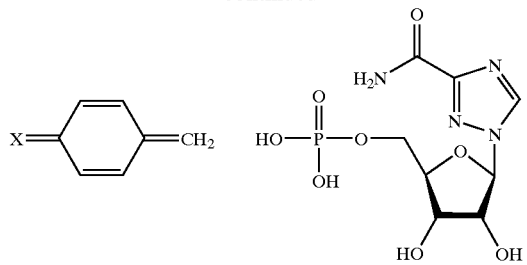

It should still further be appreciated that where nucleotides are employed in the above synthetic schemes, the nucleotide may also be modified in the phosphate group. Particularly preferred phosphate group modifications include replacement of an oxygen (and most preferably a non-ester forming oxygen) with another atom or group. For example, the double bond oxygen in the phosphate group may be replaced with a double bonded sulfur atom to form a phosphothioate. There are numerous methods of synthesizing phosphothioate nucleotides, and all of such methods are considered suitable for use herein (see e.g., DeClerq, E.; Eckstein, F.; and Merigan, T.C. Science (1969), 165, 1137, which is incorporated by reference herein).

In another example, the single bonded non-ester forming oxygen may be replace with a $BH_3$ group, and exemplary synthetic routes for preparation of boranophosphate nucleotides are described by Sood, A. et al. in J. Am. Chem. Soc. (1990), 112, 9000, by Sergueev, et al. in J. Am. Chem. Soc. (1998), 120, 9417, or by Krzyzanowska, B. et al. in Tetrahedron (1998), 54, 5119, all of which are which are incorporated by reference herein.

Contemplated Uses

It is contemplated that compounds according to Formulae 1–7, their prodrugs and/or metabolites will be used to treat a wide variety of conditions, and in fact any condition which responds positively to administration of one or more of the compounds. Among other things it is specifically contemplated that compounds of the invention may be used to treat an infection, an infestation, a cancer or tumor or an autoimmune disease. It is further contemplated that the compounds of the invention may be used to target conditions or diseases in specific organs of a patient, such as the liver or heart.

Infections contemplated to be treated with the compounds of the present invention include respiratory syncytial virus (RSV), hepatitis B virus (HBV), hepatitis C virus (HCV), herpes simplex type 1 and 2, herpes genitalis, herpes keratitis, herpes encephalitis, herpes zoster, human immunodeficiency virus (HIV), influenza A virus, hantann virus (hemorrhagic fever), human papilloma virus (HPV), measles, and fungus.

Infestations contemplated to be treated with the compounds of the present invention include protozoan infestations, as well as helminth and other parasitic infestations.

Cancers or tumors contemplated to be treated include those caused by a virus, and the effect may involve inhibiting the transformation of virus-infected cells to a neoplastic state, inhibiting the spread of viruses from transformed cells to other normal cells and/or arresting the growth of virus-transformed cells.

Autoimmune and other diseases contemplated to be treated include arthritis, psoriasis, bowel disease, juvenile diabetes, lupus, multiple sclerosis, gout and gouty arthritis, rheumatoid arthritis, rejection of transplantation, giant cell arteritis, allergy and asthma.

Still other contemplated uses of the compounds according to the present invention include use as intermediates in the chemical synthesis of other nucleoside or nucleotide analogs that are, in turn, useful as therapeutic agents or for other purposes.

In yet another aspect, a method of treating a mammal comprises administering a therapeutically and/or prophylactically effective amount of a pharmaceutical containing a compound of the present invention. In this aspect the effect may relate to modulation of some portion of the mammal's immune system, especially modulation of lymphokines profiles of Type 1 and Type 2 with respect to one another. Where modulation of Type 1 and Type 2 lymphokines occurs, it is contemplated that the modulation may include suppression of both Type 1 and Type 2, or suppression of Type 1 and stimulation of Type 2.

In general, the most preferred uses according to the present invention are those in which the active compounds are relatively less cytotoxic to the non-target host cells and relatively more active against the target. In this respect, it may also be advantageous that L-nucleosides may have increased stability over D-nucleosides, which could lead to better pharmacokinetics. This result may be attained because L-nucleosides may not be recognized by enzymes, and therefore may have longer half-lives.

It is contemplated that compounds according to the present invention will be administered in any appropriate pharmaceutical formulation, and under any appropriate protocol. Thus, administration may take place orally, parenterally (including subcutaneous injections, intravenous, intramuscularly, by intrasternal injection or infusion techniques), by inhalation spray, or rectally, topically and so forth, and in dosage unit formulations containing conventional non-toxic pharmaceutically acceptable carriers, adjuvants, and vehicles.

By way of example, it is contemplated that compounds according to the present invention can be formulated in admixture with a pharmaceutically acceptable carrier. For example, the compounds of the present invention can be administered orally as pharmacologically acceptable salts. Because the compounds of the present invention are mostly water soluble, they can be administered intravenously in a physiological saline solution (e.g., buffered to a pH of about 7.2 to 7.5). Conventional buffers such as phosphates, bicarbonates or citrates can be used for this purpose. Of course, one of ordinary skill in the art may modify the formulations within the teachings of the specification to provide numerous formulations for a particular route of administration without rendering the compositions of the present invention unstable or compromising their therapeutic activity. In particular, the modification of the present compounds to render them more soluble in water or another vehicle, for example, may be easily accomplished by minor modifications (salt formulation, esterification, etc.) that are well within the ordinary skill in the art. It is also well within the ordinary skill of the art to modify the route of administration and dosage regimen of a particular compound in order to manage the pharmacokinetics of the present compounds for maximum beneficial effect in patients.

In certain pharmaceutical dosage forms, the pro-drug form of the compounds, especially including phosphonated prodrug forms, acylated (acetylated or other) derivatives, esters and pyridine esters and various salt forms of the present compounds are preferred and can be administered in a method of treatment of a patient's condition. One of ordinary skill in the art will recognize how to readily modify the present compounds to pro-drug forms to facilitate delivery of active compounds to a target site within the host organism or patient. One of ordinary skill in the art will also take advantage of the favorable pharmacokinetic parameters of the pro-drug forms, where applicable, in delivering the present compounds to a targeted site within the host organism or patient to maximize the intended effect of the compound.

The formation of desirable prodrug compounds takes place through the modification of either the sugar portion or the base portion of the nucleoside. The sugar and/or the base portions can be modified by 1) placing substituents at different positions on the sugar or base of the compound; 2) placing different chemical substituents, or ligands, at a particular position on the sugar or base of the compound; and/or 3) designing the substituent placement and makeup around the target desired, such as the liver, brain or stomach, thus creating a "target-specific" compound.

Substituents, or ligands, can be placed at different positions on the sugar or base of the compound. In preferred embodiments, the substituents or ligands can be placed on the 3, 4, 5, or 5' position of the sugar portion of the nucleoside. In other preferred embodiments, the substituents or ligands can be placed on the base portion of the nucleoside to modify the base portion of the nucleoside without disrupting the aromaticity, or in conjugation within the purine or pyrimidine base rings.

Different chemical substituents, or ligands, can be covalently linked to a particular position on the sugar and/or base of the compound. The ligands or substituents can comprise components that are designed to be drugs or components that are designed to be non-drugs. The ligands or substituents can also comprise components that are designed to be active components or inert components. The ligands or substituents can also be designed to comprise a certain size or length, or even to reflect a specific polarity. Contemplated ligands include alkyl, alkylene, alcohols, amines, amides, sulfones, sulfides, esters, ketones, carboxylic acids, metal ions, transition metal ions, aromatic compounds, heterocyclic aromatic compounds, cyclic compounds, heterocyclic compounds, and heteroacyclic compounds.

The prodrug form of the nucleoside can also be designed to be "target-specific", meaning that the entire composition of the molecule, including additional substituents or ligands, has been designed to target a particular part of a patient, such as the liver, brain, or stomach. The prodrug form of the nucleoside can also be modified or designed to become reactive or to react intracellularly or extracellularly.

Apart from the above mentioned prodrugs and their contemplated biotransformation schemes, the present invention includes the following combination therapies according to the present invention, which comprise the administration of at least one compound of the present invention or a functional derivative thereof and at least one other pharmaceutically active ingredient. The active ingredient(s) and pharmaceutically active agents may be administered separately or together and when administered separately this may occur simultaneously or separately in any order. The amounts of the active ingredient(s) and pharmaceutically active agent(s) and the relative timings of administration will be selected in order to achieve the desired combined therapeutic effect. Preferably, the combination therapy involves the administration of one compound of the present invention or a physiologically functional derivative thereof and one of the agents mentioned herein below.

Examples of other drugs or active ingredients contemplated to be effective in combination with a modulator selected from Formula 1 or Formula 2 are anti-viral agents such as interferon, including but not limited to interferon α and γ, Ribavirin, acyclovir, and AZT™; anti-fungal agents such as tolnaftate, Fungizone™, Lotrimin™, Mycelex™, Nystatin and Amphoteracin; anti-parasitics such as Mintezol™, Niclocide™, Vermox™, and Flagyl™; bowel agents such as Immodium™, Lomotil™ and Phazyme™; anti-tumor agents such as interferon α and γ, Adriamycin™, Cytoxan™, Imuran™, Methotrexate, Mithracin™, Tiazofurin™, Taxol™; dermatologic agents such as Aclovate™, Cyclocort™, Denorex™, Florone™, Oxsoralen™, coal tar and salicylic acid; migraine preparations such as ergotamine compounds; steroids and immunosuppresants not listed above, including cyclosporins, Diprosone™, hydrocortisone; Floron™, Lidex™, Topicort and Valisone; and metabolic agents such as insulin, and other drugs which may not nicely fit into the above categories, including cytokines such as IL2, IL4, IL6, IL8, IL10 and IL12. Especially preferred primary drugs are AZT, 3TC, 8-substituted guanosine analogs, 2,3-dideoxynucleosides, interleukin II, interferons such as IαB-interferons, tucaresol, levamisole, isoprinosine and cyclolignans.

Examples of such further therapeutic agents include agents that are effective for the modulation of immune systems or associated conditions such as AZT, 3TC, 8-substituted guanosine analogs, 2', 3'-dideoxynucleosides, interleukin II, interferons, such as α-interferon, tucaresol, levamisole, isoprinosine and cyclolignans. Certain compounds according to the present invention may be effective for enhancing the biological activity of certain agents according to the present invention by reducing the metabolism or inactivation of other compounds and as such, are co-administered for this intended effect.

With respect to dosage, one of ordinary skill in the art will recognize that a therapeutically effective amount will vary with the infection or condition to be treated, its severity, the treatment regimen to be employed, the pharmacokinetics of the agent used, as well as the patient (animal or human) being treated. It is contemplated that various alternative dosages are also appropriate, including dosages between 0.5 mg/kg and 0.1 mg/kg and less, but also between 0.5 and 1.0 mg/kg and more. It is further contemplated that while treatment success may be achieved with some viral infections at relatively low plasma concentrations of the compounds of Formula 1 or Formula 2, other viral infections may require relatively high dosages. It is contemplated, however, that an appropriate regimen will be developed by administering a small amount, and then increasing the amount until the side effects become unduly adverse, or the intended effect is achieved. (FIGS. 1 and 2)

Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal and suppository administration, among other routes of administration.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavouring agents, preservatives, colouring agents and the like may be used. For solid oral preparations such as powders, tablets, capsules, and for solid preparations such as suppositories, suitable carriers and additives including starches, sugar carrier, such as dextrose, mannitol, lactose and related carriers, diluents, granulating agents, lubricants, binders, disintegrating agents and the like may be used. If desired, the tablets or capsules may be enteric-coated or sustained release by standard techniques.

For parenteral formulations, the carrier will usually comprise sterile water or aqueous sodium chloride solution, though other ingredients including those that aid dispersion may be included. Of course, where sterile water is to be used and maintained as sterile, the compositions and carriers must also be sterilized. Injectable-suspensions may also be prepared, in which case appropriate liquid carriers, suspending agents and the like may be employed.

EXAMPLES

5'-Substituted Triazole Nucleosides

To a stirred solution of the product of formula 4 (for preparation see below) (1.2 g) in dry pyridine (60 ml) at 0° C. was added DMAP (100 mg). To this cold stirred solution at 0° C. under argon was added TBDMSiCl (0.53 g) dissolved in dry pyridine (10 ml) slowly during the course of 30 min. After the addition, the reaction was stirred at 0° C. for 1 h and at RT for 12 h. It was evaporated to dryness. The residue was dissolved in EtOAc (150 ml), washed with water (70 ml) and brine (60 ml), dried and evaporated to dryness. The residue was purified by flash chromatography over silica gel using $CHCl_3 \rightarrow$ acetone as the eluent. The pure fractions were collected and concentrated to give an oily residue. Yield 1.3 g (83%).

A mixture of the above product (3.3 g), benzaldehyde dimethyl acetal (10 ml) and $ZnCl_2$ in dry $CH_2Cl_2$ (100 ml) was allowed to stir at RT under argon for 12 h. The reaction mixture was loaded on top of a silica column packed in hexanes. The column was eluted with $CHCl_3$ (200 ml) followed by $CHCl_3 \rightarrow$ EtOAc. The pure fractions were pooled and evaporated to give product 1 as foam. Yield 2.6 g (67%).

The product 1 (3.8 g) from the above reaction was dissolved in dry $CH_2Cl_2$ (50 ml) and treated with $Et_3N.3HF$ (5.5 g). The reaction was stirred at RT for 3 h and evaporated to dryness. The residue was dissolved in EtOAc (200 ml)/water (100 ml) and extracted in EtOAc. The organic extract was washed with brine (100 ml), dried and concentrated. The residue was purified by flash chromatography over silica gel using $CHCl_3 \rightarrow$ acetone as the eluent. The pure fractions were collected and concentrated to give an oily residue. Yield 2.0 g (66%).

A mixture of the above product (465 mg), Z-Valine (251 mg) and DMAP (122 mg) in dry DMF (20 ml) was allowed to stir at RT under argon for 30 min. To this stirred solution was added DCC (226 mg) and the stirring continued at RT for 2 days. The reaction was filtered and the filtrate evaporated to dryness. The residue was purified by flash chromatography over silica gel using $CHCl_3 \rightarrow$ EtOAc as the eluent. The pure fractions were pooled and concentrated to give 300 mg (44%) of product 2.

A mixture of the above product 2 (340 mg), p-toluene sulfonic acid (190 mg) and Pd/C (10%, 100 mg) in MeOH (25 ml) was hydrogenated at 45 psi for 12 h. The catalyst was filtered, washed with MeOH (20 ml), and the filtrate evaporated to dryness. The residue was triturated with dry CH$_3$CN several times and evaporated to dryness to give product 3 as a foam.

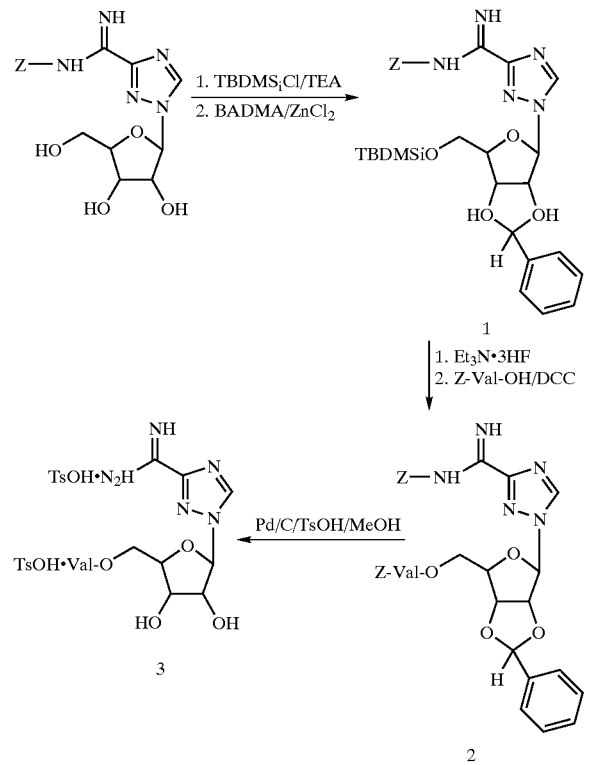

N-Modified Carboxamidine-5'-Acylated Triazole Nucleosides

To a stirred solution of the product of formula 4 (for synthesis see below) (3.77 g) in dry pyridine (60 ml) at 0° C., was added Ac$_2$O (1.08 g) dissolved in dry pyridine (10 ml) drop by drop during the course of 30 min under N$_2$ atmosphere. The stirring was continued at 0° C. for 3 h and evaporated to dryness. The residue on purification by flash chromatography over silica gel provided the required product as foam. Yield 2.1 g (50%).

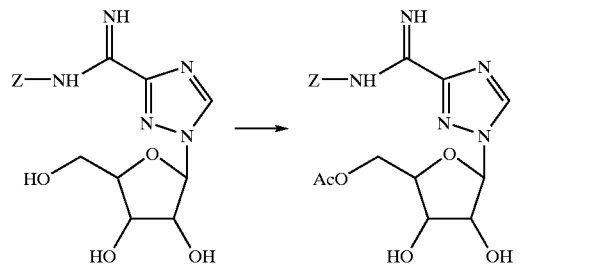

N-Modified Carboxamidine Triazole Nucleosides

To a stirred suspension of 1-β-D-ribofuranosyl-1,2,4-triazole-3-carboxamidine hydrochloride (J. T. Witkowski et al., *J. Med. Chem.*, 16, 935 (1973))(5.58 g) in dry DMF (60 ml) was added TEA (2.02 g), followed by benzyl-4-nitrophenyl carbonate (1.55 g) and the stirring continued at room temperature under an inert atmosphere for 1.5 h. The reaction mixture was evaporated to dryness. The residue was purified by flash chromatography over silica gel using chloroform→MeOH as the eluent. The pure fractions were collected and evaporated to give a white solid. Yield 6.3 g (84%). Using the same procedure para-hydroxy protected benzyl chloroformate will give the corresponding benzyl derivative.

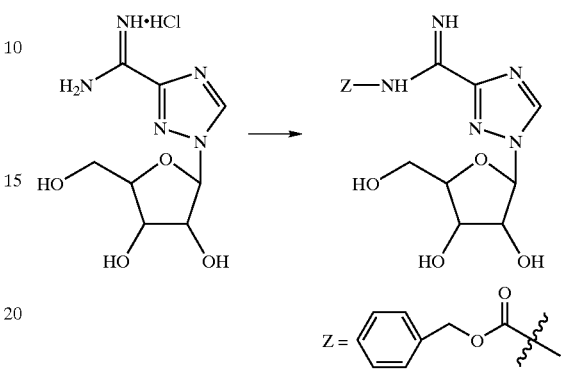

In further particularly preferred aspects, where the triazole comprises a carboxamidine moiety, it is contemplated that the carboxamidine moiety may be reacted with a carbonate to form the corresponding carbamate. Surprisingly, the inventors discovered that such reactions may be performed under conditions similar to those reported above without need for addition of protecting groups. In such exemplary reactions, D- or L-viramidine is reacted in dry DMF in the presence of triethylamine with a desired carbonate to form the corresponding carbamate, and exemplary carbamates are depicted below.

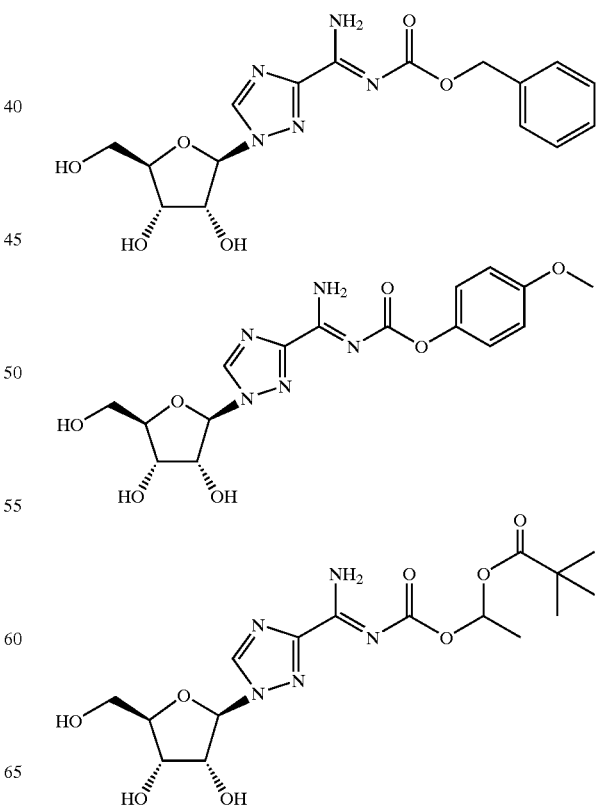

-continued

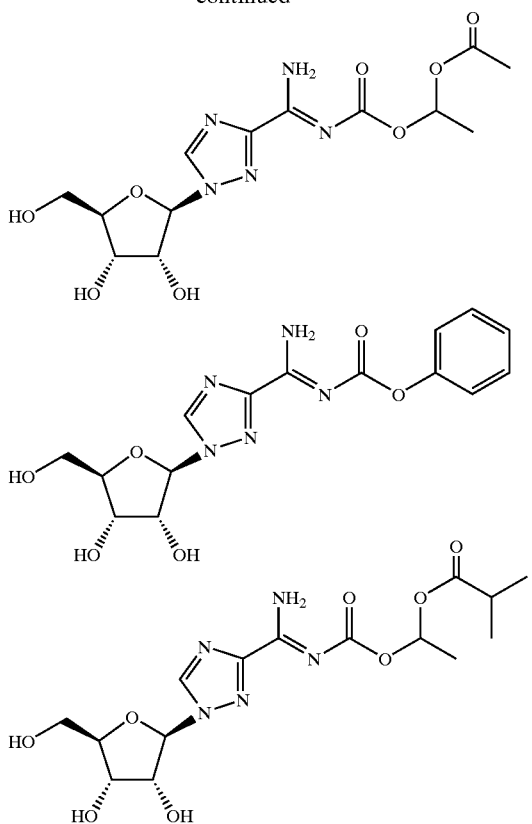

It should be especially recognized that such carbamates may act as prodrugs in which hydrolysis of the carbamate group will produce the corresponding carboxamidine. In especially preferred aspects, such prodrugs will be cleaved in a cell/organ specific manner.

N-Modified Carboxamidine Triazole Nucleotides

To a stirred solution of the product of formula 4 (1 g) in trimethyl phosphate (20 ml) at 0° C., was added phosphorus oxychloride (1 ml) under argon. The reaction mixture was stirred at 0° C. for 4 h, diluted with water (20 ml) and washed with $CH_2Cl_2$ (2×50 ml). The aqueous solution was evaporated under reduced pressure. The residue was dissolved in a minimum amount of 1N $NH_4HCO_3$ solution and applied to a Dowex×8 column ($HCO_3^-$ form). The column was eluted with water followed by the $NH_4HCO_3$ solution. The pure fractions were collected and lyophilized to give a pure compound as ammonium salt. Yield 200 mg.

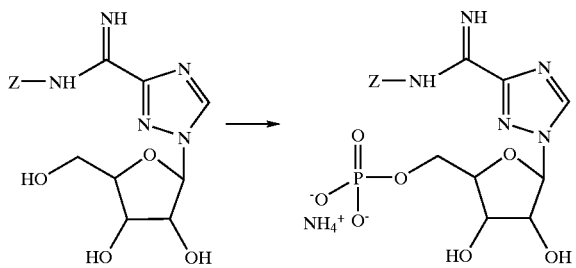

Pharmacologically Acceptable Salts of Triazole Nucleosides

A mixture of 3-cyano-1,2,4-triazole (9.41 g), 1,2,3,5-tetra-O-acetyl-β-ribofuranose (31.8 g) and bis(p-nitrophenyl)phosphate (100 mg) was placed in a preheated oil bath at 160° C. The reaction mixture was allowed to stir at that temperature under reduced pressure for 30 min while removing the released acetic acid into an ice-cold trap. After a 30 min period, the reaction was cooled and treated with ethyl acetate (200 ml) and sat. $NaHCO_3$ solution (100 ml), and extracted in ethyl acetate. The organic layer was washed with brine (100 ml), dried over anhydrous $Na_2SO_4$ and evaporated to dryness. The residue on crystallization from ether provided 28 g (80%) of the required product.

A mixture of the above product (2.5 g), $NH_4Cl$ (0.39 g), and anhydrous ammonia (70 ml) was heated in a steel bomb at 80° C. for 12 h. The bomb was cooled to −35° C., opened carefully and evaporated to dryness. The residue was co-operated with dry EtOH (50 ml). The resulting solid was treated with acetone (50 ml), triturated and filtered. The solid was re-crystallized from hot EtOH as colorless crystals. Yield 1.75 g (88%).

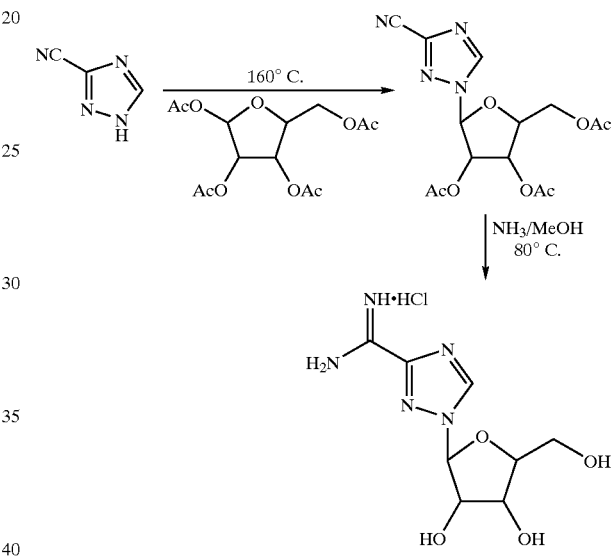

Diazole Nucleosides

Fusing ethyl pyrazole-3-carboxylate with 1,2,3,5-tetra-O-acetyl-β-L-ribofuranose in the presence of iodine as described in J. Org. Chem., USSR (Engl. Transl.), 10, 1802 (1974) will provide corresponding nucleoside 1 (see above) which on treatment with methanolic ammonia will yield the amide 2. The amide 2 will be transformed to the amidine hydrochloride 3 using the procedure reported in J. Med. Chem., 32, 1447 (1989).

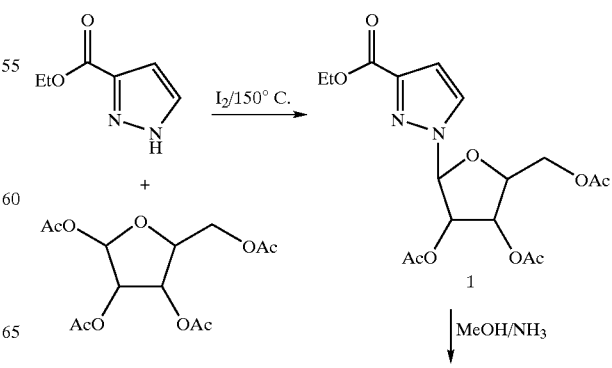

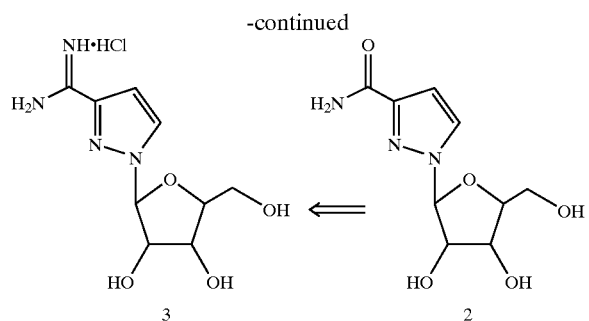

Thiazole Nucleosides

To a stirred solution of 1-O-acetyl-2,3,5-tri-O-benzoyl-β-L-ribofuranose (12.6 g) in dry $CH_2Cl_2$ (125 ml) at 0° C. under argon, was added TMSCN (3.72) followed by $SnCl_4$ in $CH_2Cl_2$ (1.0 ml in 1.0 ml of dry $CH_2Cl_2$) over a period of 30 min. The reaction mixture was allowed to stir at 0–5° C. for 4 h and quenched with 10% NaOH solution. The organic layer was separated, washed with water (100 ml) and brine (100 ml), and evaporated to dryness. The residue was purified by silica gel chromatography using as $CH_2Cl_2$ eluent to give 7.47 g (63%) of 2.

To a suspension of the above cyano sugar 2 (6.10 g) in dry ethanol (105 ml) was passed $H_2S$ for 10 min. To this solution was added DMAP (158 mg). The reaction was cooled to 10–20° C. and saturated with $H_2S$ during a 3 h period. The reaction mixture was closed with a stopper and the stirring continued at RT for 12 h. Excess $H_2S$ was removed by bubbling air into the reaction solution and the solution evaporated to dryness. The residue was purified by flash chromatography over silica gel using hexane→EtOAc as the eluent to afford 6.22 g (93%) of 3.

To a stirred suspension of the above thioamide 3 (5.05 g) in dry DMF (100 ml) at 0° C. under argon, was added $NaHCO_3$ (8.4 g) followed by ethyl bromopyruvate (3.75 ml) slowly during 30 min period. After the addition, the reaction was stirred at 0° C. for 5 h and cooled to 15° C. Lutidine (6.96 ml) and trifluoroacetic anhydride (4.16 ml) in dry DMF (20 ml) was added slowly. The reaction mixture was stirred for additional 1 h at −15° C. and filtered. The filtrate was evaporated to dryness and dissolved in $CH_2Cl_2$ (200 ml). The organic layer was washed with salt. $NaHCO_3$ solution (100 ml) and brine (100 ml), dried over anhydrous $Na_2SO_4$ and evaporated to dryness. Further purification by flash chromatography over silica gel using hexane→EtOAc gave 5.96 g (99%) of nucleoside 4.

6.0 g of the above nucleoside 4 was allowed to stir in a steel bomb for 12 h with methanolic ammonia (125 ml). The reaction vessel was cooled, opened and the contents evaporated to dryness. The residue was triturated with toluene (2×100 ml) and discarded. The remaining residue was dissolved in dry EtOH and allowed to cool in a freezer to provide 2 g (77%) of 5: mp 145–147° C. The above amide 5 from example 11 can be transformed to the amidine hydrochloride 6 using the procedure reported in J. Med. Chem., 32, 1447 (1989).

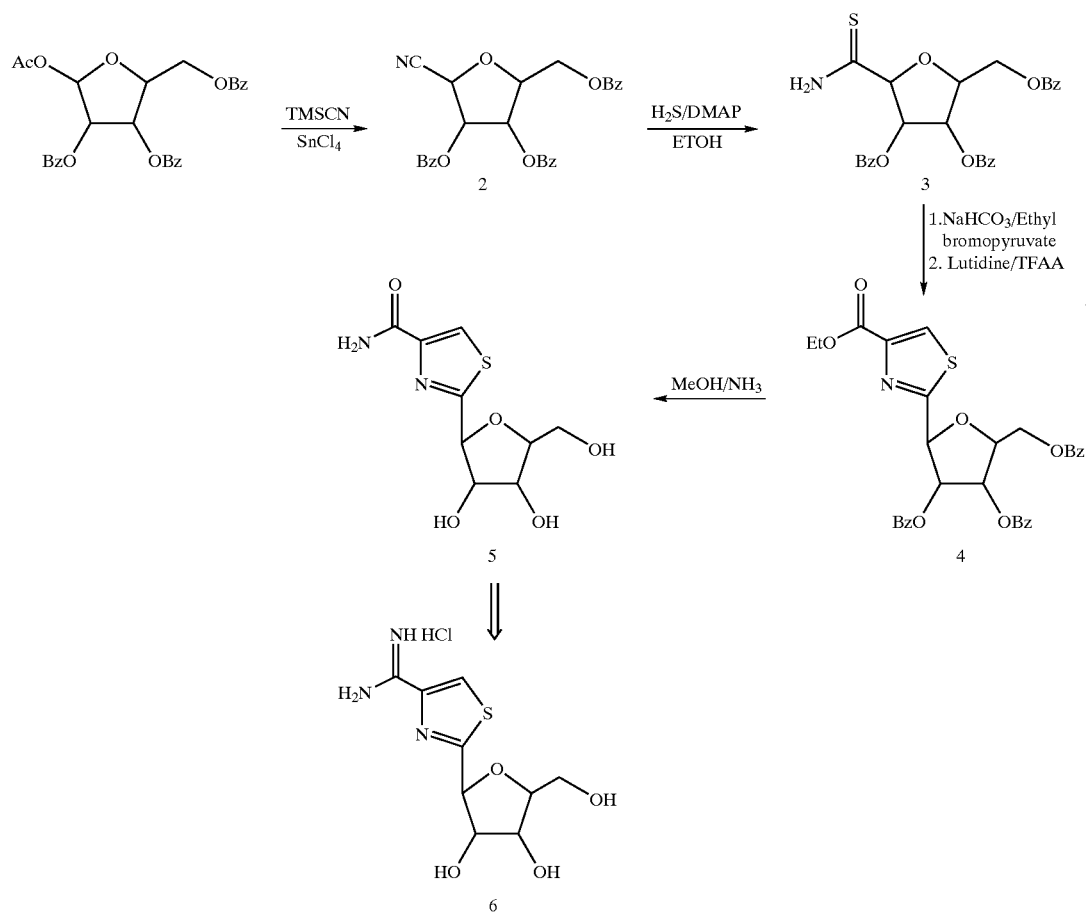

5'-Alpha-Borano-Triphosphates

A representative alpha-P-boranophosphate-substituted-5'-triphosphate nucleoside, e.g., alpha-P-borano-ribavirin-5'-triphosphate can been synthesized following a procedure essentially described by Wittkowski et al. (RE29,835) to obtain the triazole nucleoside, which is then phosphorylated in an enzymatic or non-enzymatic reaction with appropriate kinases under conditions well known in the art (e.g., Wray et al., in Antimicrob. Agents Chemother. (1986), January; 29(1): 67–72; or Wray et al. in Antiviral Res. (1985), February; 5(1): 39–48). To introduce the $BH_3$ group into the nucleotide, the corresponding Ribavirin 5'-phosphoramidite may be reacted with an amine-borane in an exchange reaction in which the suitably protected (e.g., acetylated) nucleotide is phosphitylated by (2-cyanoethyl)(N,N-diisopropyl)phosphoramidic chloride to the respective 5'-phosphoramidite derivative. The 5'-phosphoramidite is then treated in situ with excess pyridine-borane in DMF at 45–50 degree C. for about 24 h. After ammoniacal treatment, the Ribavirin-5'-borano-N,N-diisopropylphosphoramidate triphosphate can be isolated by ion-exchange column chromatography. Reaction of these phosphoramidate derivatives with excess bis-tri-n-butylammonium pyrophosphate will yield (after ion-exchange chromatographic purification) a mixture of alpha-P-borane-substituted Ribavirin-5'-triphosphate diastereoisomers in overall yields of 5–6%. The diastereoisomers may then be separated by HPLC.

Of course it should be recognized that this method of synthesis may also be applied to other triazole and non-triazole nucleosides/nucleotides for preparation of the respective alpha-borano phosphorylated nucleoside/nucleotide. It should still further be recognized that the so prepared boranophosphate nucleotide may further be modified according to the procedures above (using phosphate protecting groups as appropriate), and contemplated modifications include addition of one or more groups, as well as removal of one or more groups (e.g., gamma and/or beta phosphate group).

Synthesis Of Modified Triazole Nucleoside Phosphates Having A Cyclic Moiety

Modified triazole nucleoside phosphates with a cyclic moiety can be prepared by reaction of the corresponding phosphodichloridate and an alcohol (Khamnei, et. al., J. Med. Chem., 1996, 39: 4109). For example, the reaction of a phosphodichloridate with substituted 1,3-diols in the presence of base (such as pyridine, triethylamine, etc.) yields the desired triazole nucleoside phosphates with cyclic moiety as shown below

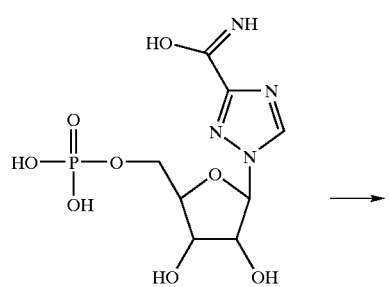

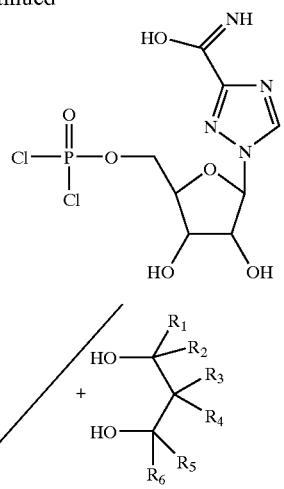

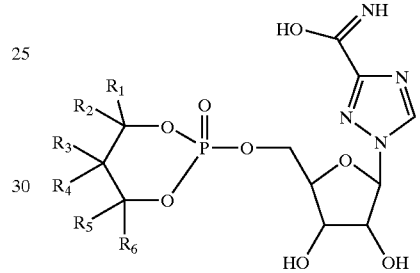

(wherein $R_1$—$R_1$ may independently substituted or unsubstituted alkyl, alkenyl, alkynyl, aryl, or halogen). Such reactive dichloridate intermediates, can be prepared from the corresponding acids and the chlorinating agents, e.g., thionyl chloride (Starrett, et al, J. Med. Chem., 1994, 1857), oxalyl chloride (Stowell, et al, Tetrahedron Lett., 1990, 31: 3261), and phosphorus pentachloride (Quast, et al, Synthesis, 1974, 490). Alternatively, these dichlorophosphonates can also be generated from disilyl esters (Bhongle, et al, Synth. Commun., 1987, 17:1071) and dialkyl esters (Still, et al, Tetrahedron Lett., 1983, 24: 4405; Patois, et al, Bull. Soc. Chim. Fr., 1993, 130: 485).

Thus, specific embodiments and applications of nucleoside analog prodrugs have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

We claim:

1. A nucleoside analog of Formula 1, in which the sugar is either in the L- or D-configuration:

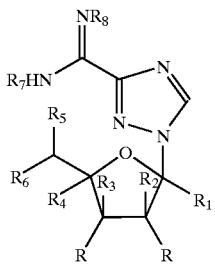

Formula 1 wherein Z is O, $CH_2$, or S;

R is independently H, hydroxyl, protected hydroxyl or halogen;

$R_1$, $R_2$, $R_3$, $R_4$, $R_5$, are independently selected from H, halogen, CN, $CH_2OH$, lower alkyl, vinyl, and acetylene radical; with the proviso that
when $R_2$ is hydroxyl, then, R that is attached to the same carbon as that of $R_2$ is not halogen;
when $R_3$ is hydroxyl, then, R that is attached to the same carbon as that of $R_3$ is not halogen;

$R_6$ is O-monoboranophosphate radical, O-diboranophosphate radical, O-triboranophosphate radical, O-monoboranophosphate derivative radical, O-diboranophosphate derivative radical, or O-triboranophosphate derivative radical;

$R_7$ is selected from H, alkyl, $CH_3COO$—, $CH_3COO$-phenyl-$CH_2$—O—CO—, phenyl, —$(CH_2)$n-COOH, coumarinic acid, salicylic acid, dithiosuccinoyl derivative radical, reductase mediated cleavable group, phosphonoformic acid radical, and phosphoramidate group radical;

$R_8$ is selected from H, H*HCl, H*HBr, lower alkyl, phenyl, $CH_3COO$—, $CH_3COO$—Phenyl-$CH_2$—O—CO—, carbamate, and phenyl; and wherein the nucleoside analog optionally forms a pharmacologically acceptable salt with an acid or a base.

2. A nucleoside analog of Formula 2, in which the sugar is either in the L- or D-configuration:

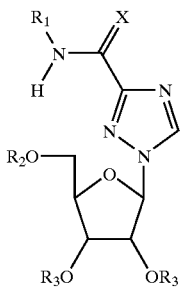

Formula 2 wherein X is O or NH;

$R_1$ is a masking group of the amino group;

$R_2$ is monoboranophosphate radical, diboranophosphate radical, triboranophosphate radical, monoboranophosphate derivative radical, diboranophosphate derivative radical, triboranophosphate derivative radical, monophosphate radical, diphosphate radical, triphosphate radical, stabilized monophosphate radical, stabilized diphosphate radical, or stabilized triphosphate radical;

$R_3$ is independently H or $C_1$–$C_{18}$ acyl; and wherein the nucleoside analog optionally forms a pharmacologically acceptable salt with an acid or a base.

3. The nucleoside analog of claim 2 having a structure according to Formula 3:

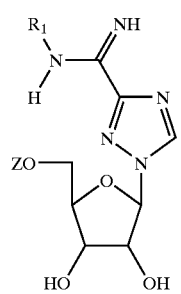

Formula 3 where $R_1$ is a masking group having any of the following structures:

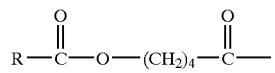

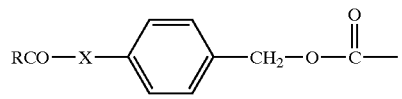

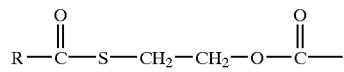

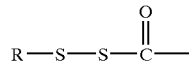

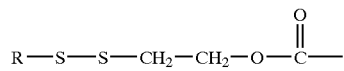

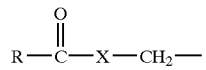

where X is O or S;

Z is $R_2$ is monoboranophosphate radical, diboranophosphate radical, triboranophosphate radical, stabilized monophosphate radical, stabilized diphosphate radical, or stabilized triphosphate radical;

R is straight or branched $C_1$–$C_{18}$ alkyl, alkenyl, alkynyl, aryl, or aralkyl; and wherein the nucleoside analog optionally forms a pharmacologically acceptable salt with an acid or a base.

4. A nucleoside analog of Formula 4, in which the sugar is either in the L- or D-configuration:

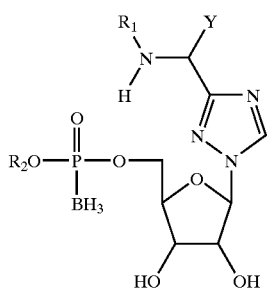

Formula 4 wherein Y is O or NH;

wherein $R_1$ is H or a masking group as designated in claim 3;

$R_2$ is H, phosphate radical to form a diphosphate, diphosphate radical to form a triphosphate, or a masking group of the phosphate having any of the following structures:

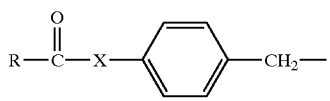

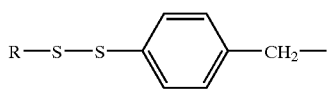

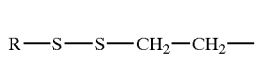 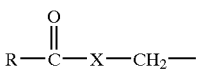

where X is O, or S;

R is straight or branched $C_1$–$C_{18}$ alkyl, alkenyl, alkynyl, aryl, or aralkyl; and wherein the nucleoside analog optionally forms a pharmacologically acceptable salt with an acid or a base.

5. A nucleoside analog of Formula 5, in which the sugar is either in the L- or D-configuration:

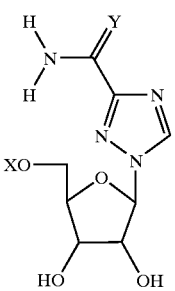

Formula 5 wherein Y is O or NH;

wherein X is $R_2$ is monoboranophosphate radical, diboranophosphate radical, triboranophosphate radical, monoboranophosphate derivative radical, diboranophosphate derivative radical, triboranophosphate derivative radical, stabilized monophosphate radical, stabilized diphosphate radical, or stabilized triphosphate radical; and wherein the nucleoside analog optionally forms a pharmacologically acceptable salt with an acid or a base.

6. A nucleoside analog of Formula 6, in which the sugar is either in the L- or D-configuration:

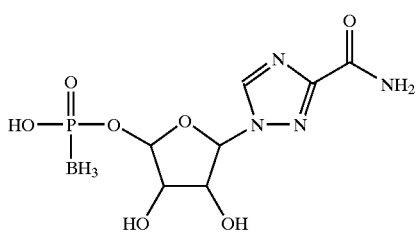

Formula 6 wherein the nucleoside analog optionally forms a pharmacologically acceptable salt with an acid or a base.

* * * * *